United States Patent
Long et al.

(10) Patent No.: US 7,329,752 B2
(45) Date of Patent: Feb. 12, 2008

(54) CARBAMATE COMPOUNDS AS 5-HT$_4$ RECEPTOR AGONISTS

(75) Inventors: Daniel D. Long, San Francisco, CA (US); Seok-Ki Choi, Palo Alto, CA (US); Paul R. Fatheree, San Francisco, CA (US); Adam A. Goldblum, Berkeley, CA (US); Daniel Marquess, Half Moon Bay, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 11/602,888

(22) Filed: Nov. 21, 2006

(65) Prior Publication Data

US 2007/0117796 A1 May 24, 2007

Related U.S. Application Data

(60) Provisional application No. 60/738,702, filed on Nov. 22, 2005.

(51) Int. Cl.
*A61K 31/439* (2006.01)
*A61K 31/541* (2006.01)
*C07D 401/12* (2006.01)
*C07D 417/14* (2006.01)

(52) U.S. Cl. .................. 546/126; 544/58.5; 514/228.2; 514/304

(58) Field of Classification Search .................. 546/126
See application file for complete search history.

(56) References Cited

U.S. PATENT DOCUMENTS

| | | | |
|---|---|---|---|
| 5,223,511 | A | 6/1993 | Turconi et al. |
| 5,753,673 | A | 5/1998 | Ohuchi et al. |
| 6,002,009 | A | 12/1999 | Cereda et al. |
| 6,117,882 | A | 9/2000 | Schaus et al. |
| 6,281,218 | B1 | 8/2001 | Cereda et al. |
| 2002/0173505 | A1 | 11/2002 | Skogvall |
| 2005/0148573 | A1 | 7/2005 | Katsu et al. |
| 2005/0197335 | A1 | 9/2005 | Marquess et al. |
| 2005/0228014 | A1 | 10/2005 | Marquess et al. |
| 2006/0100236 | A1 | 5/2006 | Choi et al. |
| 2006/0100426 | A1 | 5/2006 | Choi et al. |
| 2006/0135764 | A1 | 6/2006 | Fatheree et al. |
| 2006/0276482 | A1 | 12/2006 | Gendron et al. |

FOREIGN PATENT DOCUMENTS

EP 0 309 423 A2 3/1989
IT 01298271 B1 12/1999

OTHER PUBLICATIONS

Baxter et al., "Bezimidazolone derivatives act as 5-HT$_4$ receptor ligands in rat oesophagus", European Journal of Pharmacology, 212, pp. 225-229 (1992).
Dumuis et al., "Characterization of a novel 5-HT$_4$ receptor antagonist of the azabicycloalkyl benzimidazolone class: DAU 6285", Naunyn-Schmiedeberg's Arch Pharmacol, 345, pp. 264-269 (1992).
Dumuis et al., "Azabicycloalkyl benzimidazolone derivatives as a novel class of potent agonists at the 5-HT$_4$ receptor positively coupled to adenylate cyclase in brain", Naunyn-Schmiedeberg's Arch Pharmacol, 343, pp. 245-251 (1991).
Schaus et al., "Synthesis and structure—activity relationships of potent and orally active 5-HT4 receptor antagonists: indazole and benzimidazolone derivaties", Journal of Medicinal Chemistry, 41(11) pp. 1943-1955 (1998).
Tapia et al., "2,3-Dihydro-2-oxo-1H-benzimidazole-1-carboxamides with Selective Affinity for the 5-HT$_4$ Receptor: Synthesis and Structure-Affinity and Structure-Activity Relationships of a New Series of Partial Agonist and Antagonist Derivatives", J. Med. Chem., 42, pp. 2870-2880 (1999).
Turconi et al., "Azabicycloalkyl benzimidazolones: Interaction with serotonergic 5-HT$_3$ and 5-HT$_4$ receptors and potential therapeutic implications", Drugs of the Future, 16(11), pp. 1011-1026 (1991).
Turconi et al., "Synthesis of a New Class of 2,3-Dihydro-2-oxo-1H-benzimidazole-1-carobxylic Acid Derivatives as Highly Potent 5-HT$_3$ Receptor Antagonists", J. Med. Chem., 33, pp. 2101-2108 (1990).

*Primary Examiner*—Laura L. Stockton
(74) *Attorney, Agent, or Firm*—Jeffrey A. Hagenah; Roberta P. Saxon

(57) ABSTRACT

The invention provides novel benzoimidazolone-carboxamide-derived carbamate 5-HT$_4$ receptor agonist compounds of formula (I):

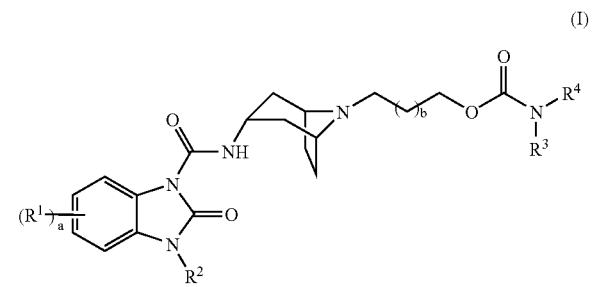

(I)

wherein $R^1$, $R^2$, $R^3$, $R^4$, a, and b are defined in the disclosure. The invention also provides pharmaceutical compositions comprising such compounds, methods of using such compounds to treat diseases associated with 5-HT$_4$ receptor activity, and processes and intermediates useful for preparing such compounds.

13 Claims, No Drawings

CARBAMATE COMPOUNDS AS 5-HT$_4$ RECEPTOR AGONISTS

CROSS-REFERENCE TO RELATED APPLICATIONS

This application claims the benefit of U.S. Provisional Application No. 60/738,702 filed on Nov. 22, 2005, the disclosure of which is incorporated herein by reference in its entirety.

BACKGROUND OF THE INVENTION

1. Field of the Invention

The invention is directed to benzoimidazolone-carboxamide-derived carbamate compounds which are useful as 5-HT$_4$ receptor agonists. The invention is also directed to pharmaceutical compositions comprising such compounds, methods of using such compounds for treating or preventing medical conditions mediated by 5-HT$_4$ receptor activity, and processes and intermediates useful for preparing such compounds.

2. State of the Art

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. There has been, therefore, substantial interest in developing therapeutic agents that target specific 5-HT receptor subtypes.

In particular, characterization of 5-HT$_4$ receptors and identification of pharmaceutical agents that interact with them has been the focus of significant recent activity. (See, for example, the review by Langlois and Fischmeister, *J. Med. Chem.* 2003, 46, 319-344.) 5-HT$_4$ receptor agonists are useful for the treatment of disorders of reduced motility of the gastrointestinal tract. Such disorders include irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-HT$_4$ receptor agonist compounds may be used in the treatment of central nervous system disorders including cognitive disorders, behavioral disorders, mood disorders, and disorders of control of autonomic function.

Despite the broad utility of pharmaceutical agents modulating 5-HT$_4$ receptor activity, few 5-HT$_4$ receptor agonist compounds are in clinical use at present.

Accordingly, there is a need for new 5-HT$_4$ receptor agonists that achieve their desired effects with minimal side effects. Preferred agents may possess, among other properties, improved selectivity, potency, pharmacokinetic properties, and/or duration of action.

SUMMARY OF THE INVENTION

The invention provides novel compounds that possess 5-HT$_4$ receptor agonist activity. Among other properties, compounds of the invention have been found to be potent and selective 5-HT$_4$ receptor agonists. In addition, compounds of the invention have been found to exhibit favorable pharmacokinetic properties which are predictive of good bioavailability upon oral administration.

Accordingly, the invention provides a compound of formula (I):

(I)

wherein:
R$^1$ is halo or C$_{1-3}$alkyl, wherein C$_{1-3}$alkyl is optionally substituted with hydroxy or halo;
R$^2$ is hydrogen or C$_{1-3}$alkyl, wherein C$_{1-3}$alkyl is optionally substituted with hydroxy;
R$^3$ is C$_{1-3}$alkyl or hydrogen;
R$^4$ is —(CH$_2$)$_{1-3}$C(O)NR$^a$R$^b$, or R$^3$ and R$^4$ together with the nitrogen atom to which they are attached form a moiety selected from:
(i) a moiety of formula (a):

(a)

(ii) a moiety of formula (b):

(b)

(iii) a moiety of formula (c):

(c)

wherein:
R$^5$ is —OC(O)NR$^a$R$^b$, —C(O)NR$^a$R$^b$, —NR$^d$S(O)$_2$C$_{1-3}$alkyl, —NR$^d$C(O)R$^c$, —NR$^d$S(O)$_2$NR$^a$R$^b$, or —NR$^d$C(O)OR$^e$;
R$^6$ is —C(O)R$^f$, —(CH$_2$)$_2$OR$^g$, —S(O)$_2$NR$^a$R$^b$, —S(O)$_2$C$_{1-3}$alkyl, or —S(O)$_2$(CH$_2$)$_{1-3}$S(O)$_2$C$_{1-3}$alkyl;
R$^a$, R$^b$, and R$^c$ are independently hydrogen or C$_{1-3}$alkyl;

$R^d$ is hydrogen or $C_{1-3}$alkyl, wherein $C_{1-3}$alkyl is optionally substituted with hydroxy;
$R^e$ is $C_{1-3}$alkyl;
$R^f$ is hydrogen, $C_{1-3}$alkyl, tetrahydrofuranyl, or —$NR^aR^b$;
$R^g$ is hydrogen or $C_{1-3}$alkyl;
a is 0, 1 or 2;
b is 0, 1, 2 or 3;
c is 0, 1, or 2;
d is 1 or 2; and
e is 1 or 2;
provided that when c is 0, then d is 2, and $R^5$ is —C(O)$NR^aR^b$; and when c is 2, then d is 1;
or a pharmaceutically-acceptable salt or solvate or stereoisomer thereof.

The invention also provides a pharmaceutical composition comprising a compound of the invention and a pharmaceutically-acceptable carrier.

Further, the invention provides a method of treating a disease or condition associated with 5-HT$_4$ receptor activity, e.g. a disorder of reduced motility of the gastrointestinal tract, the method comprising administering to the mammal, a therapeutically effective amount of a compound or of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new 5-HT$_4$ receptor agonists, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with 5-HT$_4$ receptor activity, e.g. a disorder of reduced motility of the gastrointestinal tract, in a mammal.

DETAILED DESCRIPTION OF THE INVENTION

The invention provides novel benzoimidazolone-carboxamide-derived carbamate 5-HT$_4$ receptor agonists of formula (I), or pharmaceutically-acceptable salts or solvates or stereoisomers thereof. The following substituents and values are intended to provide representative examples of various aspects of this invention. These representative values are intended to further define such aspects and are not intended to exclude other values or limit the scope of the invention.

In specific aspects of the invention, $R^1$ is halo or $C_{1-3}$alkyl; or $R^1$ is fluoro, chloro, bromo, or methyl.

In a specific aspect, $R^2$ is hydrogen.

In another specific aspect, $R^2$ is $C_{1-3}$alkyl, wherein $C_{1-3}$alkyl is optionally substituted with hydroxy.

In yet another specific aspect, $R^2$ is hydrogen or $C_{1-3}$alkyl.

In other specific aspects of the invention, $R^2$ is methyl, ethyl, propyl, or isopropyl; $R^2$ is ethyl or isopropyl; or $R^2$ is isopropyl.

In specific aspects, $R^3$ is $C_{1-3}$alkyl; $R^3$ is methyl or ethyl; or $R^3$ is methyl.

In a specific aspect, $R^4$ is —$(CH_2)_{1-3}C(O)NR^aR^b$.

In another specific aspect, $R^4$ is

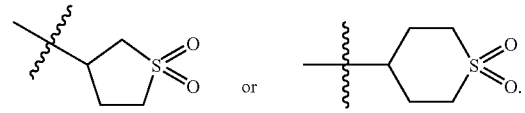

In yet another specific aspect, $R^4$ is —$(CH^2)_{1-3}C(O)NR^aR^b$ or

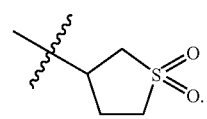

In a specific aspect of the invention, $R^3$ and $R^4$ together with the nitrogen atom to which they are attached form a moiety selected from a moiety of formula (a), a moiety of formula (b), and a moiety of formula (c).

In a specific aspect, $R^3$ and $R^4$ together with the nitrogen atom to which they are attached form a moiety of formula (a). In another specific aspect, $R^3$ and $R^4$ together with the nitrogen atom to which they are attached form a moiety of formula (a) wherein $R^5$ is —OC(O)$NR^aR^b$ or —C(O)$NR^aR^b$.

In a specific aspect, $R^3$ and $R^4$ together with the nitrogen atom to which they are attached form a moiety of formula (b). In other specific aspects, $R^3$ and $R^4$ together with the nitrogen atom to which they are attached form a moiety of formula (b), wherein $R^6$ is —C(O)$R^f$, —$(CH_2)_2OR^g$, or —S(O)$_2NR^aR^b$; or $R^6$ is —C(O)$R^f$, and e is 1.

In still another aspect of the invention, $R^3$ and $R^4$ together with the nitrogen atom to which they are attached form a moiety of formula (c).

In specific aspects, $R^a$, $R^b$, $R^c$, $R^d$, and $R^g$ are independently hydrogen, methyl, or ethyl; or $R^a$, $R^b$, $R^c$, $R^d$, and $R^g$ are independently hydrogen or methyl.

In specific aspects, $R^e$ is methyl or ethyl; or $R^e$ is methyl.

In specific aspects, $R^f$ is $C_{1-3}$alkyl, tetrahydrofuranyl, or —$NR^aR^b$; or $R^f$ is methyl, tetrahydrofuranyl, or —$NR^aR^b$.

In another specific aspect, $R^f$ is tetrahydrofuranyl.

In other specific aspects, $R^f$ is $C_{1-3}$alkyl, or $R^f$ is methyl.

In yet another specific aspect, $R^f$ is —$NR^aR^b$, wherein $R^a$ and $R^b$ are as defined herein.

In specific aspects, a is 0 or 1; or a is 0 or 2. In another specific aspect, a is 0.

In specific aspects, b is 0, 1, or 2; or b is 1 or 2. In another specific aspect, b is 1.

In a specific aspect, c is 1 or 2. In another specific aspect, c is 1.

In a specific aspect, d is 1.

In a specific aspect, e is 1.

In one aspect, the invention provides a compound of formula (I) wherein c is 1 or 2; d is 1; and e is 1.

In another aspect, the invention provides a compound of formula (I) wherein:
$R^3$ is $C_{1-3}$alkyl; and
$R^4$ is —$(CH_2)_{1-3}C(O)NR^aR^b$ or

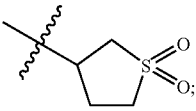

or R³ and R⁴ together with the nitrogen atom to which they are attached form a moiety selected from a moiety of formula (a), a moiety of formula (b), and a moiety of formula (c);
wherein:
R⁵ is —OC(O)NR$^a$R$^b$ or —C(O)NR$^a$R$^b$; and
R⁶ is —C(O)R$^f$, —(CH$_2$)$_2$OR$^g$, or —S(O)$_2$NR$^a$R$^b$.

In still another aspect, the invention provides a compound of formula (I) wherein R³ and R⁴ together with the nitrogen atom to which they are attached form a moiety selected from a moiety of formula (a), a moiety of formula (b), and a moiety of formula (c); wherein:
R⁵ is —C(O)NR$^a$R$^b$ or —C(O)NR$^a$R$^b$;
R⁶ is —C(O)R$^f$, —(CH$_2$)$_2$OR$^g$, or —S(O)$_2$NR$^a$R$^b$;
R$^a$, R$^b$, and R$^g$ are independently hydrogen or methyl;
R$^f$ is methyl, tetrahydrofuranyl, or —NR$^a$R$^b$;
c is 1 or 2; d is 1; and e is 1.

In yet another aspect, the invention provides a compound of formula (I) wherein:
R² is ethyl or isopropyl
R³ is C$_{1-3}$alkyl; and
R⁴ is —(CH$_2$)$_{1-3}$C(O)NR$^a$R$^b$ or

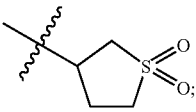

or R³ and R⁴ together with the nitrogen atom to which they are attached form a moiety selected from a moiety of formula (a), a moiety of formula (b), and a moiety of formula (c); wherein
R⁵ is —OC(O)NR$^a$R$^b$ or —C(O)NR$^a$R$^b$;
R⁶ is —C(O)R$^f$, —(CH$_2$)$_2$OR$^g$, or —S(O)$_2$NR$^a$R$^b$;
R$^a$, R$^b$, and R$^g$ are independently hydrogen or methyl;
R$^f$ is methyl, tetrahydrofuranyl, or —NR$^a$R$^b$;
a is 0; c is 1 or 2; d is 1; and e is 1.

The chemical naming conventions used herein are illustrated for the compound of Example 1:

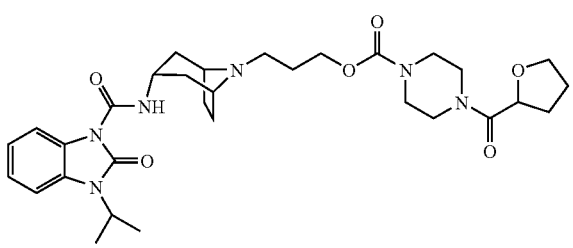

which is designated 4-(tetrahydrofuran-2-carbonyl)piperazine-1-carboxylic acid 3-{(1S,3R,5R)-3-[(3-isopropyl-2-oxo-2,3-dihydro-benzoimidazole-1-carbonyl)amino]-8-aza-[3.2.1]oct-8-yl}propyl ester, according to the AutoNom software, provided by MDL Information Systems, GmbH (Frankfurt, Germany). The designation (1S,3R,5R) describes the relative orientation of the bonds associated with the bicyclic ring system that are depicted as solid and dashed wedges. In all of the compounds of the invention depicted above, the benzoimidazolone-carboxamide is endo to the azabicyclooctane group.

Particular mention may be made of the following compounds:

4-(tetrahydrofuran-2-carbonyl)piperazine-1-carboxylic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester;

4-(2-hydroxyethyl)piperazine-1-carboxylic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester;

4-acetyl-piperazine-1-carboxylic acid 3-{(1S,3R,5R)-3-[(3-isopropyl-2-oxo-2,3 -dihydro-benzoimidazole-1-carbonyl)amino]-8-azabicyclo[3.2.1]oct-8-yl}propyl ester;

4-dimethylcarbamoyloxypiperidine-1-carboxylic acid 3-{(1S,3R,5R)-3-[(3-isopropyl-2-oxo-2,3-dihydrobenzoimidazole-1-carbonyl)amino]-8-aza-bicyclo[3.2.1]oct-8-yl}propyl ester;

3-carbamoylpiperidine-1-carboxylic acid 3-{(1S,3R,5R)-3-[(3-isopropyl-2-oxo-2,3-dihydro-benzoimidazole-1-carbonyl)amino]-8-azabicyclo[3.2.1]oct-8-yl}propyl ester;

1,1-dioxo-1λ⁶-thiomorpholine-4-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester;

(1,1-dioxotetrahydro-1λ⁶-thiophen-3-yl)methylcarbamic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester;

(R)-2-carbamoylpyrrolidine-1-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester;

4-acetyl-[1,4]diazepane-1-carboxylic acid 3-{(1S,3R,5R)-3-[(3-isopropyl-2-oxo-2,3-dihydro-benzoimidazole-1-carbonyl)amino]-8-azabicyclo[3.2.1]oct-8-yl}propyl ester;

dimethylcarbamoylmethyl-methylcarbamic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester;

4-dimethylcarbamoylpiperazine-1-carboxylic acid 3-{(1S,3R,5R)-3-[(3-isopropyl-2-oxo-2,3-dihydroben-zoimidazole-1-carbonyl)amino]-8-azabicyclo[3.2.1]oct-8-yl}propyl ester; and 4-dimethylsulfamoylpiperazine-1-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester.

As exemplified by particular compounds listed above, the compounds of the invention may contain one or more chiral centers. Accordingly, the invention includes racemic mixtures, pure stereoisomers, and stereoisomer-enriched mixtures of such isomers, unless otherwise indicated. When a particular stereoisomer is shown, it will be understood by those skilled in the art, that minor amounts of other stereoisomers may be present in the compositions of the invention unless otherwise indicated, provided that any utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Representative alkyl groups include, by way of example, methyl, ethyl, n-propyl (n-Pr), isopropyl (i-Pr), n-butyl (n-Bu), sec-butyl, isobutyl, tert-butyl, and the like.

The term "halo" means fluoro, chloro, bromo or iodo.

The term "compound" means a compound that was synthetically prepared or produced in any other way, such as by metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:
 (a) preventing the disease, disorder, or medical condition from occurring, i.e., prophylactic treatment of a patient;
 (b) ameliorating the disease, disorder, or medical condition, i.e., eliminating or causing regression of the disease, disorder, or medical condition in a patient;
 (c) suppressing the disease, disorder, or medical condition, i.e., slowing or arresting the development of the disease, disorder, or medical condition in a patient; or
 (d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), naphthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; acyloxy groups, such as acetoxy, trifluoroacetoxy and the like. The term "leaving group" further encompasses groups such as $-OC_6F_5$, $-CCl_3$, para-$OC_6H_4NO_2$, and imidazolyl.

The term "protected derivative thereof" means a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

The substituents and variables shown in the following schemes have the definitions provided herein unless otherwise indicated.

In one method of synthesis, compounds of formula (I) can be prepared as illustrated in Scheme A.

A compound of formula (III) can be prepared as shown in Scheme B below.

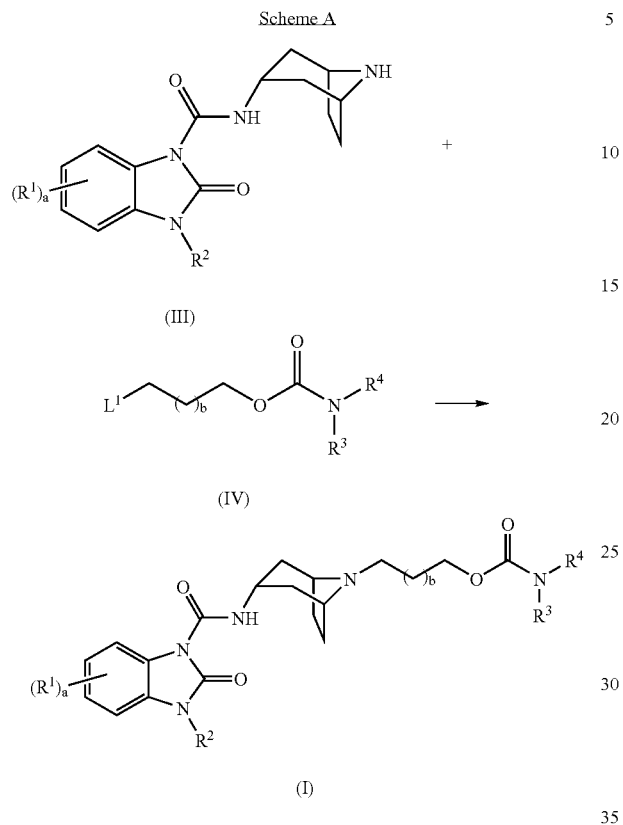

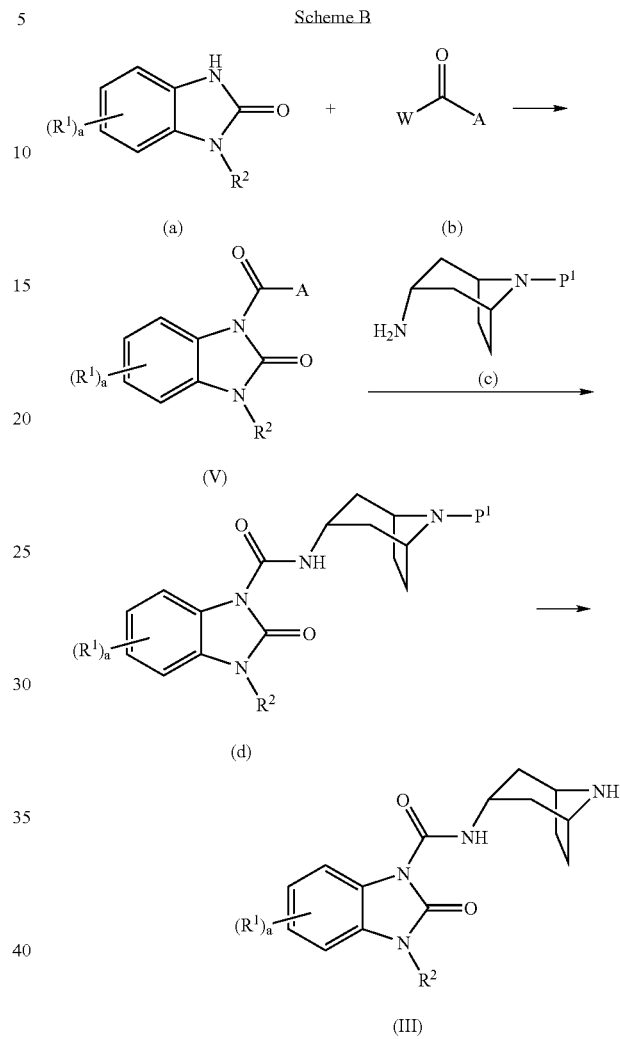

A benzoimidazolone-carboxamide tropane intermediate (III) is reacted with a compound of formula (IV), wherein $L^1$ is a leaving group, to provide a compound of formula (I). Typically, $L^1$ is an $S_N2$-favoring leaving group, such as chloro, iodo, or bromo. A compound of formula (IV) is contacted with between about 0.25 and about 1.5 equivalents of the benzoimidazolone-carboxamide tropane (III), in an inert diluent, in the presence of a base, such as N,N-diisopropylethylamine (DIPEA), and of a catalyst, such as sodium iodide. Suitable inert diluents include dimethylformamide, acetonitrile, tetrahydrofuran, N-methyl-2-pyrrolidone, and the like. Suitable bases also include, for example, triethylamine, 1,8-diazabicyclo-[5.4.0]undec-7-ene (DBU), and potassium carbonate. Suitable catalysts also include, for example, potassium iodide, and tetrabutylammonium iodide. This reaction is typically conducted at a temperature of from about 40° C. to about 100° C. for between about 2 and about 24 hours or until the reaction is substantially complete.

The product of formula (I) is isolated and purified by conventional procedures. For example, the product can be concentrated to dryness under reduced pressure, taken up in an aqueous weak acid solution and purified by high-performance liquid chromatography (HPLC).

It will be understood that in the process of Scheme A and in other processes described herein using a compound of formula (III), a compound of formula (III) can be supplied in the form of the free base or in a salt form, with appropriate adjustment of reaction conditions, as necessary, as known to those skilled in the art.

In Scheme B, intermediate (a), an optionally substituted 1,3-dihydrobenzoimidazol-2-one, is reacted with intermediate (b), wherein W is a leaving group (such as halo, i.e., fluoro, chloro, or bromo), and A is a leaving group chosen such that it reacts under different conditions than W (such as $—OC_6F_5$, $—CCl_3$, para-$OC_6H_4NO_2$, or imidazol-1-yl); or W and A are each imidazol-1-yl; to provide a compound of formula (V), which is reacted with intermediate (c), wherein $P^1$ represents an amino protecting group, such as Boc, to provide intermediate (d). The protecting group $P^1$ is removed from intermediate (d) by standard procedures to provide a compound of formula (III).

While optimum reaction conditions may vary depending on the particular reactants or solvents used, such conditions can be readily determined by one skilled in the art by routine optimization procedures.

For example, in an exemplary process using 4-nitrophenyl chloroformate as intermediate (b), the benzoimidazolone intermediate (a) is dissolved under an inert atmosphere in an inert diluent, such as tetrahydrofuran, ether, DMF, or a combination thereof, in the presence of a strong base, such as sodium hydride, lithium diisopropylamine, and n-butyl lithium, and is contacted with between about 1 and about 1.3 equivalents of 4-nitrophenyl chloroformate. The mixture is stirred at about 0° C. to about 40° C. for between about 12 and about 24 hours or until the reaction is substantially complete to form an activated ester, a compound of formula (V). The compound of formula (V) is isolated and purified, or it can be reacted, in situ, with a protected amino-tropane, intermediate (c), in the presence of an inert diluent, such as tetrahydrofuran, at a temperature of from about 30° C. to about 90° C. for between about 10 and about 24 hours to provide protected intermediate (d).

Using conventional methods, the amino-protecting group, $P^1$ is removed from intermediate (d), to provide a benzoimidazolone-carboxamide tropane compound of formula (III). A variation of the above process of preparing intermediate (III) using 4-nitrophenyl chloroformate as intermediate (b) is described in Example 13 below.

Alternatively, a compound of formula (I) can be prepared as shown in Scheme C below.

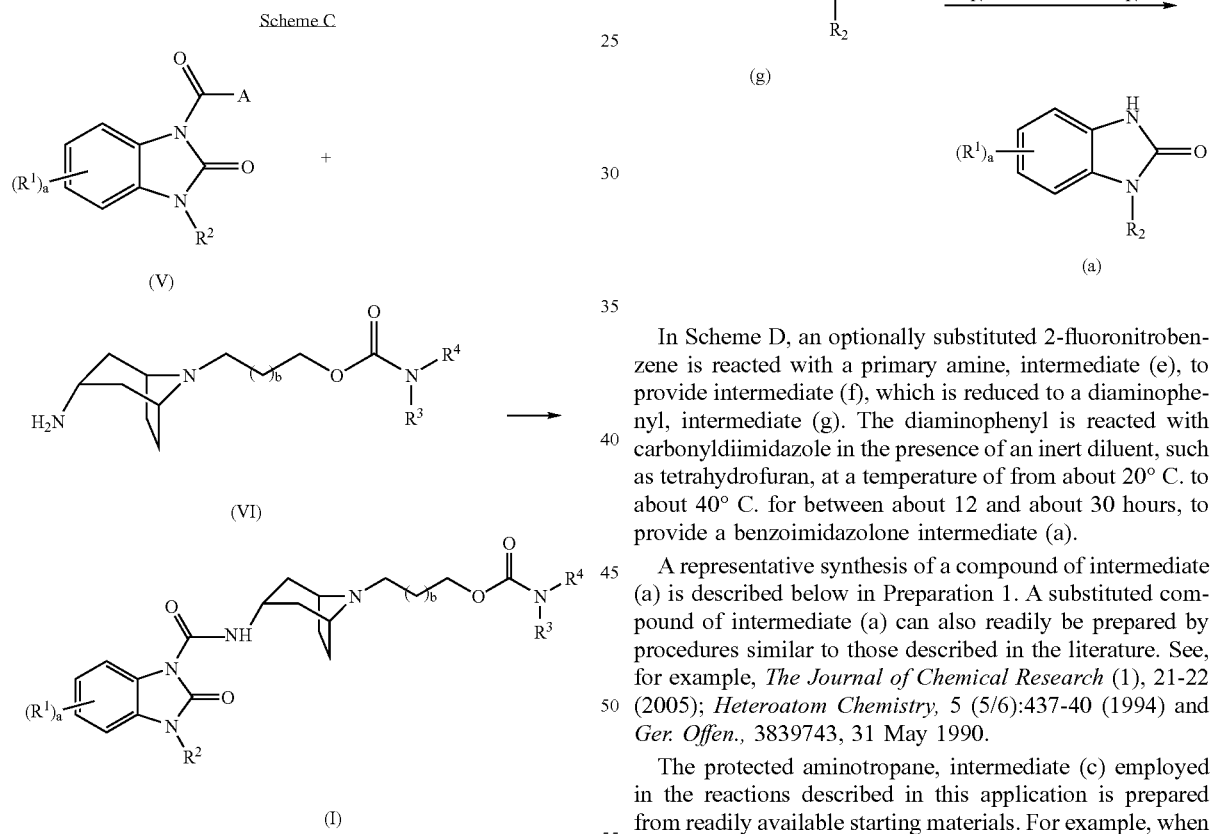

A benzoimidazolone-carboxamide intermediate (V) is reacted with a tropane-alkylene-carboxamide compound of formula (VI) to provide a compound of formula (I). The compound of formula (V), the synthesis of which is described in Scheme B, is either isolated and purified, or reacted in situ, with a compound of formula (VI), in the presence of an inert diluent, such as tetrahydrofuran, at a temperature range of from about 30° C. to about 90° C. for between about 10 and about 24 hours, or until the reaction is complete, to provide a compound of formula (I).

The benzoimidazolone intermediate (a) can be prepared as shown below in Scheme D.

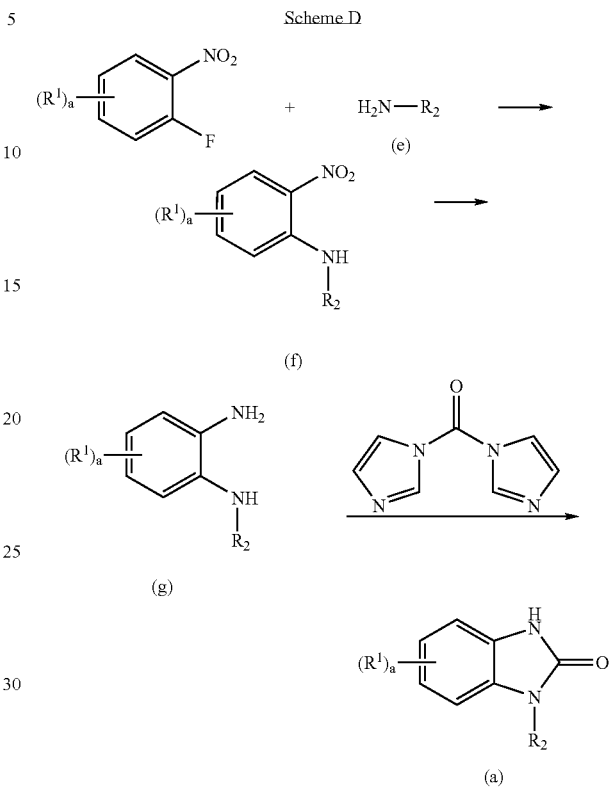

In Scheme D, an optionally substituted 2-fluoronitrobenzene is reacted with a primary amine, intermediate (e), to provide intermediate (f), which is reduced to a diaminophenyl, intermediate (g). The diaminophenyl is reacted with carbonyldiimidazole in the presence of an inert diluent, such as tetrahydrofuran, at a temperature of from about 20° C. to about 40° C. for between about 12 and about 30 hours, to provide a benzoimidazolone intermediate (a).

A representative synthesis of a compound of intermediate (a) is described below in Preparation 1. A substituted compound of intermediate (a) can also readily be prepared by procedures similar to those described in the literature. See, for example, *The Journal of Chemical Research* (1), 21-22 (2005); *Heteroatom Chemistry*, 5 (5/6):437-40 (1994) and *Ger. Offen.*, 3839743, 31 May 1990.

The protected aminotropane, intermediate (c) employed in the reactions described in this application is prepared from readily available starting materials. For example, when the amino-protecting group $P^1$ is Boc, the protected aminotropane can be prepared as shown below in Scheme E.

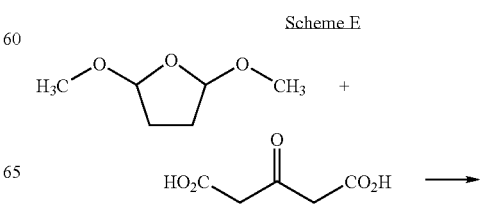

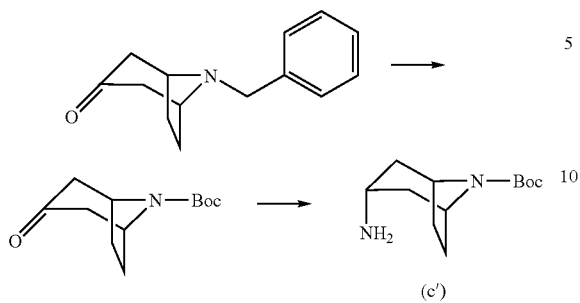

(c')

As described in detail in Preparation 2 below, to prepare the Boc-protected intermediate (c'), 2,5-dimethoxytetrahydrofuran is contacted with between about 1 and 2 equivalents of benzyl amine and a slight excess, for example about 1.1 equivalents, of 1,3-acetonedicarboxylic acid in an acidic aqueous solution in the presence of a buffering agent, such as sodium hydrogen phosphate. The reaction mixture is heated to between about 60° C. and about 100° C. to ensure decarboxylation of any carboxylated intermediates in the product, 8-benzyl-8-azabicyclo-[3.2.1]octan-3-one, commonly N-benzyltropanone.

The N-benzyltropanone intermediate is typically reacted with a slight excess of di-tert-butyl dicarbonate (commonly (Boc)$_2$O), for example, about 1.1 equivalents, under a hydrogen atmosphere in the presence of a transition metal catalyst to provide 3-oxo-8-azabicyclo[3.2.1]octane-8-carboxylic acid tert-butyl ester. The reaction is typically conducted at ambient temperature for about 12 to about 72 hours. Finally, 3-oxo-8-azabicyclo[3.2.1]octane-8-carboxylic acid tert-butyl ester is contacted with a large excess, for example at least about 25 equivalents, of ammonium formate in an inert diluent, such as methanol, in the presence of a transition metal catalyst to provide the product, intermediate (c), in the endo configuration with high stereospecificity, for example endo to exo ratio of >99:1. The reaction is typically conducted at ambient temperature for about 12 to about 72 hours or until the reaction is substantially complete. It is advantageous to add the ammonium formate reagent in portions. For example, 3-oxo-8-azabicyclo[3.2.1] octane-8-carboxylic acid tert-butyl ester is contacted with an initial portion of ammonium formate of about 15 to about 25 equivalents. After an interval of about 12 to about 36 hours, an additional portion of about 5 to about 10 equivalents of ammonium formate is added. The subsequent addition can be repeated after a similar interval. The product, intermediate (c), can be purified by conventional procedures, such as alkaline extraction.

A compound of formula (IV) can be easily prepared by standard procedures from common starting materials, as described below in Scheme F.

Scheme F

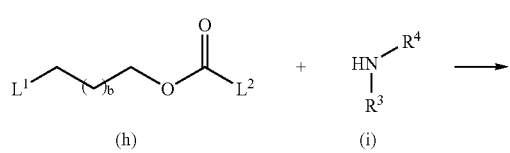

(h)                (i)

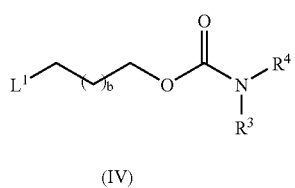

(IV)

In Scheme F, intermediate (h), wherein L$^1$ and L$^2$ are leaving groups, is reacted with a secondary amine (i) to provide a compound of formula (IV). The secondary amine (i) is dissolved in an inert diluent, such as dichloromethane, and intermediate (h) is added, in the presence of a base, such as N,N-diisopropylethylamine, at a temperature ranging from about 0° C. to about 40° C., for about 30 minutes to about 4 hours. The product, a compound of formula (IV), can be purified by conventional procedures, such as by HPLC.

Typically, L$^1$ and L$^2$ are halo leaving groups, such as chloro, iodo, bromo; mesylate can also be used as leaving group L$^1$. Suitable bases can include, for example, triethyl amine, DBU, and potassium carbonate. Suitable inert diluents can include acetonitrile, tetrahydrofuran, and N,N-dimethylformamide.

Intermediate compounds of formula (h) and (i) are available commercially or can be synthesized from readily available starting materials. The synthesis of many secondary amines, i.e., intermediate compounds of formula (i) that can be used in Scheme F, are described in the Examples section herein.

A compound of formula (VI) can be prepared as shown in Scheme G.

Scheme G

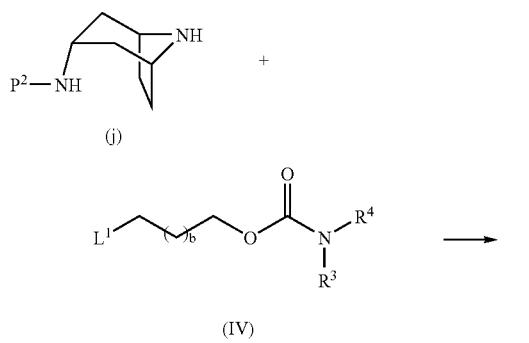

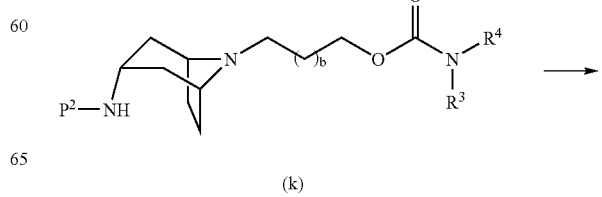

(k)

-continued

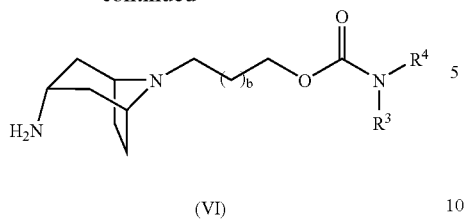

(VI)

In Scheme G, intermediate (j), wherein $P^2$ is an amino-protecting group, is reacted with a compound of formula (IV) to provide protected intermediate (k), which is then deprotected to provide a compound of formula (VI). The reaction of Scheme G is typically conducted under the amine coupling conditions described above for the reaction of Scheme A.

A compound of formula (j) can be prepared by protecting the amino nitrogen of the protected aminotropane intermediate (c), with an amino-protecting group $P^2$ and then removing $P^1$ from the nitrogen of the azabicyclooctane group. Protecting groups $P^1$ and $P^2$ are chosen such that they are removed under different conditions. For example, when $P^1$ is chosen as Boc, then Cbz can be used as $P^2$. The protecting group Boc is typically removed by treatment with an acid, such as trifluoroacetic acid, providing the acid salt of the intermediate. The acid salt of the intermediate can be converted to the free base, if desired, by conventional treatment with base. The protecting group Cbz is conveniently removed by hydrogenolysis over a suitable metal catalyst such as palladium on carbon. Further details regarding specific reaction conditions and other procedures for preparing representative compounds of the invention or intermediates thereto are described in the examples below.

Accordingly, in a method aspect, the invention provides a process for preparing a compound of formula (I) or a salt or solvate or stereoisomer thereof, wherein $R^1$, $R^2$, $R^3$, $R^4$, a, and b are as defined herein, the process comprising:

(a) reacting a compound of formula (III):

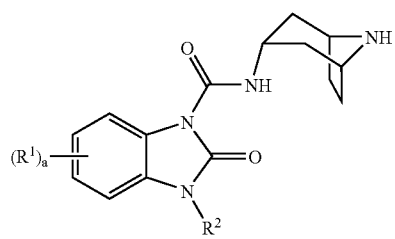

(III)

with a compound of formula (IV):

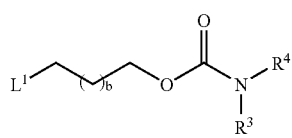

(IV)

wherein $L^1$ is a leaving group; or (b) reacting a compound of formula (V):

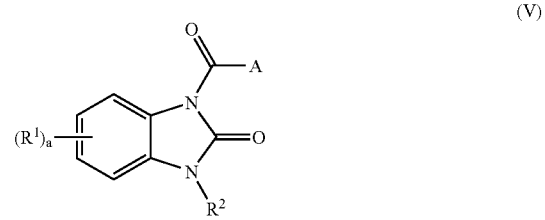

(V)

wherein A is a leaving group;
with a compound of formula (VI):

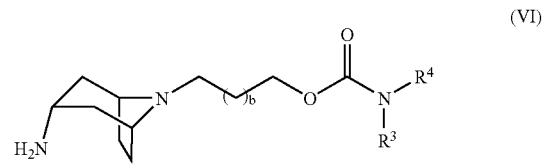

(VI)

to provide a compound of formula (I), or a salt or solvate or stereoisomer thereof.

In additional embodiments, this invention is directed to the other processes described herein; and to the products prepared by any of the processes described herein.

Pharmaceutical Compositions

The benzoimidazolone-carboxamide-derived carbamate compounds of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in Remington: *The Science and Prac-* tice of Pharmacy, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (such as cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

FORMULATION EXAMPLE A

Hard gelatin capsules for oral administration are prepared as follows:

| Ingredients | Amount |
| --- | --- |
| Compound of the invention | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

FORMULATION EXAMPLE D

Tablets for oral administration are prepared as follows:

| Ingredients | Amount |
| --- | --- |
| Compound of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

FORMULATION EXAMPLE F

Single-scored tablets for oral administration are prepared as follows:

| Ingredients | Amount |
| --- | --- |
| Compound of the invention | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of compositions per tablet).

FORMULATION EXAMPLE G

A suspension for oral administration is prepared as follows:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

FORMULATION EXAMPLE H

A dry powder for administration by inhalation is prepared as follows:

| Ingredients | Amount |
| --- | --- |
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

FORMULATION EXAMPLE I

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

FORMULATION EXAMPLE J

An injectable formulation is prepared as follows:

| Ingredients | Amount |
| --- | --- |
| Compound of the invention | 0.2 g |
| Sodium acetate buffer solution (0.4 M) | 40 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

FORMULATION EXAMPLE K

Capsules for oral administration are prepared as follows:

| Ingredients | Amount |
| --- | --- |
| Compound of the Invention | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

FORMULATION EXAMPLE L

Capsules for oral administration are prepared as follows:

| Ingredients | Amount |
| --- | --- |
| Compound of the Invention | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

It will be understood that any form of the compounds of the invention, (i.e. free base, pharmaceutical salt, or solvate) that is suitable for the particular mode of administration, can be used in the pharmaceutical compositions discussed above.

Utility

The benzoimidazolone-carboxamide-derived carbamate compounds of the invention are 5-$HT_4$ receptor agonists and therefore are expected to be useful for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

In particular, the compounds of the invention increase motility of the gastrointestinal (GI) tract and thus are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by 5-HT$_4$ receptors, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-HT$_4$ receptors will range from about 0.0007 to about 20 mg/kg/day of active agent, including from about 0.0007 to about 1 mg/kg/day. For an average 70 kg human, this would amount to from about 0.05 to about 70 mg per day of active agent.

In one aspect of the invention, the compounds of the invention are used to treat chronic constipation. When used to treat chronic constipation, the compounds of the invention will typically be administered orally in a single daily dose or in multiple doses per day. Preferably, the dose for treating chronic constipation will range from about 0.05 to about 70 mg per day.

In another aspect of the invention, the compounds of the invention are used to treat irritable bowel syndrome. When used to treat constipation-predominant irritable bowel syndrome, the compounds of the invention will typically be administered orally in a single daily dose or in multiple doses per day. Preferably, the dose for treating constipation-predominant irritable bowel syndrome will range from about 0.05 to about 70 mg per day.

In another aspect of the invention, the compounds of the invention are used to treat diabetic gastroparesis. When used to treat diabetic gastroparesis, the compounds of the invention will typically be administered orally in a single daily dose or in multiple doses per day. Preferably, the dose for treating diabetic gastroparesis will range from about 0.05 to about 70 mg per day.

In yet another aspect of the invention, the compounds of the invention are used to treat functional dyspepsia. When used to treat functional dyspepsia, the compounds of the invention will typically be administered orally in a single daily dose or in multiple doses per day. Preferably, the dose for treating functional dyspepsia will range from about 0.05 to about 70 mg per day.

The invention also provides a method of treating a mammal having a disease or condition associated with 5-HT$_4$ receptor activity, the method comprising administering to the mammal a therapeutically effective amount of a compound of the invention or of a pharmaceutical composition comprising a compound of the invention.

Since compounds of the invention are 5-HT$_4$ receptor agonists, such compounds are also useful as research tools for investigating or studying biological systems or samples having 5-HT$_4$ receptors, or for discovering new 5-HT$_4$ receptor agonists. Moreover, since compounds of the invention exhibit binding selectivity for 5-HT$_4$ receptors as compared with binding to receptors of other 5-HT subtypes, particularly 5-HT$_3$ receptors, such compounds are particularly useful for studying the effects of selective agonism of 5-HT$_4$ receptors in a biological system or sample. Any suitable biological system or sample having 5-HT$_4$ receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like.

In this aspect of the invention, a biological system or sample comprising a 5-HT$_4$ receptor is contacted with a 5-HT$_4$ receptor-agonizing amount of a compound of the invention. The effects of agonizing the 5-HT$_4$ receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of analogs of guanosine triphosphate (GTP), such as [$^{35}$S]GTPγS (guanosine 5'-O-(γ-thio)triphosphate) or GTP-Eu, into isolated membranes via receptor catalyzed exchange of GTP analogs for GDP analogs, ligand-mediated changes in free intracellular calcium ions (measured, for example, with a fluorescence-linked imaging plate reader or FLIPR® from Molecular Devices, Inc.), and measurement of mitogen activated protein kinase (MAPK) activation. A compound of the invention may agonize or increase the activation of 5-HT$_4$ receptors in any of the functional assays listed above, or assays of a similar nature. A 5-HT$_4$ receptor-agonizing amount of a compound of the invention will typically range from about 1 nanomolar to about 500 nanomolar.

Additionally, the compounds of the invention can be used as research tools for discovering new 5-HT$_4$ receptor agonists. In this embodiment, 5-HT$_4$ receptor binding or functional data for a test compound or a group of test compounds is compared to the 5-HT$_4$ receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to be potent agonists of the 5-HT$_4$ receptor and to exhibit substantial selectivity for the 5-HT$_4$ receptor subtype over the 5-HT$_3$ receptor subtype in radioligand binding assays. Further, representative compounds of the invention have demonstrated superior pharmacokinetic properties in a rat model. Compounds of the invention are thus expected to demonstrate good bioavailablity upon oral administration. In addition, representative compounds of the invention tested in an in vitro voltage-clamp model using isolated whole cells expressing the hERG cardiac potassium channel, have been shown not to exhibit an unacceptable level of inhibition of the potassium ion current. The voltage-clamp assay is an accepted pre-clinical method of assessing the potential for pharmaceutical agents to change the pattern of cardiac repolarization, specifically to cause, so-called QT prolongation, which has been associated with cardiac arrhythmia. (Cavero et al., *Opinion on Pharmacotherapy*, 2000, 1, 947-73, Fermini et al., *Nature Reviews Drug Discovery*, 2003, 2, 439-447) Accordingly, pharmaceutical compositions comprising compounds of the invention are expected to have an acceptable cardiac profile.

These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl
(Boc)$_2$O=di-tert-butyl dicarbonate
DCM=dichloromethane
DMF=N,N-dimethylformamide
DMSO=dimethyl sulfoxide
EtOAc=ethyl acetate
mCPBA=m-chloroperbenzoic acid
MeCN=acetonitrile
MTBE=tert-butyl methyl ether
PyBop=benzotriazol-1-yloxytripyrrolidino-phosphonium hexafluorophosphate
$R_f$=retention factor
RT=room temperature
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observation conditions. Unless otherwise indicated, mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

A general protocol for analytical HPLC: Each of crude compounds was dissolved in 50% MeCN/H$_2$O (with 0.1% TFA) at 0.5-1.0 mg/mL concentration, and was analyzed by using anal. HPLC: 1) reverse-phased anal. Column: Zorbax Bonus-RP (3.5 µm of particle size, 2.1×50 mm); 2) flow rate: 0.5 mL/min; 3) 5% MeCN/H$_2$O containing 0.1% TFA (isocratic; 0-0.5 min); 5% MeCN/H$_2$O containing 0.1% TFA to 75% MeCN/H$_2$O containing 0.1% TFA (linear gradient; 0.5-4 min); 4) detection: 214, 254, and 280 nm. Other conditions used are indicated whenever necessary.

A general protocol for preparative HPLC purification: Crude compounds were dissolved in 50% acetic acid in water at 50-100 mg/mL concentration, filtered, and fractionated using preparative HPLC: 1) column; YMC Pack-Pro C18 (50a×20 mm; ID=5 µm); 2) linear gradient: 10% A/90% B to 50% A/50% B over 30 min; 3) flow rate: 40 mL/min; 4) detection: 214 nm.

Preparation of Secondary Amines

Preparation of various secondary amines used as intermediates in the synthesis of a compound of formula (I) are described below.

The N-sulfonyl derivatives of piperazine were prepared from N-Boc piperazine by reacting with respective sulfonyl chloride (iPr$_2$NEt, CH$_2$Cl$_2$, 0° C.), and deprotecting the N-Boc group (CF$_3$CO$_2$H, CH$_2$Cl$_2$). 1-Methanesulfonylpiperazine: $^1$H-NMR (CDCl$_3$; neutral): δ (ppm) 3.1 (t, 4H), 2.9 (t, 4H), 2.7 (s, 3H). Methanesulfonylpiperazine was also prepared by reacting methanesulfonyl chloride with excess piperazine (>2 equivalents) in water.

The N-derivatives of piperazine such as 1-(dimethylaminocarbonyl)piperazine, and 1-(dimethylaminosulfonyl)piperazine were prepared by reacting piperazine with dimethylaminochloroformate, or dimethylaminosulfamoyl chloride, respectively.

The racemic or single chiral isomer forms of 3-acetylaminopyrrolidine were prepared by treating N$^1$-Boc-3-aminopyrrolidine (racemate, 3R, or 3S) with acetyl chloride (iPr$_2$NEt, CH$_2$Cl$_2$, 0° C.), and deprotecting the N-Boc group (CF$_3$CO$_2$H, CH$_2$Cl$_2$). 3-(Acetamido)pyrrolidine: $^1$H-NMR (DMSO-d$_6$; TFA salt): δ (ppm) 4.2 (quin, 1H), 3.3-3.1 (m, 3H), 2.9 (m, 1H), 2.0 (m, 1H), 1.8 (br s, 4H).

The N$^3$-alkanesulfonyl derivatives of (3R)-aminopyrrolidine were obtained by treating N$^1$-Boc-(3R)-aminopyrrolidine with propionylsulfonyl chloride or cyclohexylmethylsulfonyl chloride (i-Pr$_2$NEt, CH$_2$Cl$_2$, 0° C.), and deprotecting N-Boc group (CF$_3$CO$_2$H, CH$_2$Cl$_2$).

Derivatives of tetrahydro-3-thiophenamine-1,1-dioxide were prepared following the protocol of Loev, B. *J. Org. Chem.* 1961, 26, 4394-9 by reacting 3-sulfolene with a requisite primary amine in methanol (cat. KOH, rt). N-Methyl-3-tetrahydrothiophene-amine-1,1-dioxide (TFA salt): $^1$H-NMR (DMSO-d$_6$): δ (ppm) 9.4 (br s, 2H), 4.0-3.8 (quin, 1H), 3.6-3.5 (dd, 1H), 3.4-3.3 (m, 1H), 3.2-3.1 (m, 2H), 2.5 (s, 3H), 2.4(m, 1H), 2.1 (m, 1H).

(S)-1,1-Dioxo-tetrahydro-1λ$^6$-thiophen-3-ylamine was prepared as follows:

1) N-Boc protection of (S)-3-tetrahydrothiophenamine (Dehmlow, E. V.; Westerheide, R. *Synthesis* 1992, 10, 947-9) by treating with (Boc)$_2$O in methanol at room temperature for about 12 h; 2) oxidation by treating with mCPBA in dichloromethane to N-Boc protected (S)-1,1-dioxo-tetrahydro-1λ$^6$-thiophen-3-ylamine at 0° C. for about 5 h; and 3) N-Boc deprotection of the sulfone derivative with TFA in dichloromethane at room temperature for 1 h to the free amine which was isolated as a TFA salt. (R)-1,1-dioxo-tetrahydro-1λ$^6$-thiophen-3-ylamine was prepared using the same method, but replacing the (S)-3-tetra-hydrothiophenamine with (R)-3-tetrahydrothiophenamine.

N-Methyl-tetrahydro-2H-thiopyran-4-amine-1,1-dioxide was prepared from tetrahydro-4H-thiopyran-4-one: i) MeNH$_2$, NaBH$_4$; ii) (Boc)$_2$O, MeOH; iii) mCPBA, CH$_2$Cl$_2$, 0° C.; iv) CF$_3$CO$_2$H, CH$_2$Cl$_2$. (m/z): [M+H]$^+$ calcd for C$_6$H$_{13}$NO$_2$S 164.07; found, 164.9. $^1$H-NMR (CD$_3$OD; TFA salt): δ (ppm) 3.4-3.1 (m, 5H), 2.7 (s, 3H), 2.4 (br d, 2H), 2.1 (br m, 2H).

Proline dimethylamide, isonipecotamide (piperidine-4-carboxamide), and 1-(tetrahydro-2-furoyl)piperazine are available commercially, and were purchased from commercial sources.

4-Piperidinol-dimethylcarbamate was prepared by reacting dimethylaminochloroformate with N-Boc protected 4-piperidinol.

Preparation 1

Preparation of 1-isopropyl-1,3-dihydro-2H-benzimidazol-2-one a. Preparation of N-isopropyl-N-(2-nitrophenyl)amine To a cold solution of 2-fluoro-nitrobenzene (31.8 g, 0.225 mol) in ethanol (300 mL) cooled in an ice bath was added isopropylamine (54.0 mL, 0.634 mol), followed by the addition of a solution of potassium carbonate (31.1 g, 0.225 mol) in water (120 mL). The mixture was stirred at 0° C. for 1 h, then refluxed for 6 h. The reaction was terminated by cooling the mixture to ambient temperature, and evaporating it under reduced pressure yielding an orange residue. The residue was partitioned between ethyl ether (800 mL) and a brine solution (300 mL). The organic layer was dried and filtered, to provide the title intermediate (39 g) as an orange liquid. $^1$H-NMR (CDCl$_3$, 300 MHz): δ (ppm) 8.06 (d, 1H), 7.30 (t, 1H), 6.74 (d, 1H), 6.48 (t, 1H), 3.73 (hept, 1H), 1.20(d, 6H).

b. Preparation of N-(2-aminophenyl)-N-isopropylamine

To a mixture of ethanol (600 mL) and 2 M sodium hydroxide solution (320 mL) cooled in an ice bath was added Zn dust (59.5 g) slowly. While stirring the Zn slurry, N-isopropyl-N-(2-nitrophenyl)amine (41 g, 0.228 mol) dissolved in ethanol (50 mL) was added. The mixture was stirred at 0° C. for 30 min, then heated to 85° C. The mixture was stirred at 85° C. for about 12 h until the refluxing solution of the mixture became a colorless solution. The mixture was then cooled to 0° C. and filtered. The collected solid was rinsed with EtOAc (200 mL). The filtrate and rinsed solution were combined, and evaporated in vacuo to remove excess volatile solvents. During the concentration, the mixture became pale brown/yellow. The aqueous concentrate was extracted with EtOAc (800 mL). The organic solution was concentrated to dryness, to provide the title intermediate (33 g) as a brown-pink oil which was used in the next step without further treatment. $^1$H-NMR (CDCl$_3$, 300 MHz): δ (ppm) 6.73-6.5 (m, 4H), 3.58-3.55 (hept, 1H), 1.2 (d, 6H).

c. Preparation of 1-isopropyl-1,3-dihydro-2H-benzimidazol-2-one

To a solution of the product of step (b), N-(2-aminophenyl)-N-isopropylamine (34 g, 0.226 mol), in tetrahydrofuran (500 mL) was added carbonyldiimidazole (36.7 g, 0.226 mol) as a solid. The mixture was stirred under an atmosphere of nitrogen gas at ambient temperature for about 24 h. The mixture was concentrated in vacuo, and a resulting dark brown residue was distributed between EtOAc (700 mL) and brine solution (300 mL). The organic layer was then washed with 1 M phosphoric acid multiple times (~3×300 mL) until the color of the organic layer turned from dark brown to pale yellow. The organic solution was evaporated to dryness to provide the title intermediate (34 g) as a pale yellow oil which solidified slowly on standing. The purity of the material was assessed by $^1$H-NMR which indicated no detectable impurity: $^1$H-NMR (CD$_3$OD, 300 MHz): δ (ppm) 7.2 (m, 1H), 7.0 (m, 3H), 4.6 (hept, 1H), 1.46 (d, 6H). (m/z): [M+H]$^+$ calcd for C$_{10}$H$_{12}$N$_2$O 177.09; found 177.2.

Anal. HPLC: retention time=2.7 min (99% purity): 1) column: Zorbax, Bonus-RP, 3.5 μm of particle size, 2.1×50 mm; 2) flow rate: 0.5 mL/min; 3) isocratic condition (10% solvent B/90% solvent A) for 0 to 0.5 min; then linear gradient to 50% solvent B/50% solvent A over 5 min (solvent A=98% water/2% MeCN/0.1% TFA; solvent B=90% MeCN/10% water/0.1% TFA). TLC analysis (silica gel plate): R$_f$=0.5 (CH$_2$Cl$_2$). Liquid chromatography mass spectrometry (LCMS) (m/z): [M+H]$^+$ calcd for C$_{10}$H$_{12}$N$_2$O 177.09; found 177.3.

Preparation 2

Preparation of (1S,3R,5R)-3-amino-8-azabicyclo [3.2.1]octane-8-carboxylic acid tert-butyl ester a. Preparation of 8-benzyl-8-azabicyclo[3.2.1]octan-3-one Concentrated hydrochloric acid (30 mL) was added to a heterogeneous solution of 2,5-dimethoxy tetrahydrofuran (82.2 g, 0.622 mol) in water (170 mL) while stirring. In a separate flask cooled to 0° C. (ice bath), concentrated hydrochloric acid (92 mL) was added slowly to a solution of benzyl amine (100 g, 0.933 mol) in water (350 mL). The 2,5-dimethoxytetrahydrofuran solution was stirred for approximately 20 min, diluted with water (250 mL), and then the benzyl amine solution was added, followed by the addition of a solution of 1,3-acetonedicarboxylic acid (100 g, 0.684 mol) in water (400 mL) and then the addition of sodium hydrogen phosphate (44 g, 0.31 mol) in water (200 mL). The pH was adjusted from pH 1 to pH~4.5 using 40% NaOH. The resulting solution was stirred overnight. The solution was then acidified to pH 3 from pH 7.5 using 50% hydrochloric acid, heated to 85° C. and stirred for 2 hours. The solution was cooled to room temperature, basified to pH 12 using 40% NaOH, and extracted with DCM (3×500 mL). The combined organic layers were washed with brine, dried, filtered and concentrated under reduced pressure to produce the crude title intermediate as a viscous brown oil (52 g).

To a solution of the crude intermediate in methanol (1000 mL) was added di-tert-butyl dicarbonate (74.6 g, 0.342 mol) at 0° C. The solution was allowed to warm to room temperature and stirred overnight. The methanol was removed under reduced pressure and the resulting oil was dissolved in dichloromethane (1000 mL). The intermediate was extracted into 1 M H$_3$PO$_4$ (1000 mL) and washed with dichloromethane (3×250 mL) The aqueous layer was basified to pH 12 using aqueous NaOH, and extracted with dichloromethane (3×500 mL). The combined organic layers were dried, filtered and concentrated under reduced pressure to provide the title intermediate as a viscous, light brown oil. $^1$H-NMR (CDCl$_3$) δ (ppm) 7.5-7.2 (m, 5H, C$_6$H$_5$), 3.7 (s, 2H, CH$_2$Ph), 3.45(broad s, 2H, CH—NBn), 2.7-2.6 (dd, 2H, CH$_2$CO), 2.2-2.1 (dd, 2H, CH$_2$CO), 2.1-2.0(m, 2H, CH$_2$CH$_2$), 1.6 (m, 2H, CH$_2$CH$_2$). (m/z): [M+H]$^+$ calcd for C$_{14}$H$_{17}$NO 216.14; found, 216.0.

b. Preparation of 3-oxo-8-azabicyclo[3.2.1]octane-8-carboxylic acid tert-butyl ester To a solution of 8-benzyl-8-azabicyclo[3.2.1]octan-3-one (75 g, 0.348 mol) in EtOAc (300 mL) was added a solution of di-tert-butyl dicarbonate (83.6 g, 0.383 mol, 1.1 eq) in EtOAc (300 mL). The resulting solution and rinse (100 mL EtOAc) was added to a 1 L Parr hydrogenation vessel containing 23 g of palladium hydroxide (20 wt. % Pd, dry basis, on carbon, ~50% wet with water; e.g. Pearlman's catalyst) under a stream of nitrogen. The reaction vessel was degassed (alternating vacuum and $N_2$ five times) and pressurized to 60 psi of $H_2$ gas. The reaction solution was agitated for two days and recharged with $H_2$ as needed to keep the $H_2$ pressure at 60 psi until the reaction was complete as monitored by silica thin layer chromatography. The black solution was then filtered through a pad of Celite® and concentrated under reduced pressure to provide the title intermediate as a viscous, yellow to orange oil. It was used in the next step without further treatment. $^1$H NMR (CDCl$_3$) δ (ppm) 4.5 (broad, 2H, CH—NBoc), 2.7 (broad, 2H, CH$_2$CO), 2.4-2.3 (dd, 2H, CH$_2$CH$_2$), 2.1 (broad m, 2H, CH$_2$CO), 1.7-1.6 (dd, 2H, CH$_2$CH$_2$), 1.5 (s, 9H, (CH$_3$)$_3$COCON)).

c. Preparation of (1S,3R,5R)-3-amino-8-azabicyclo[3.2.1]octane-8-carboxylic acid tert-butyl ester To a solution of the product of the previous step (75.4 g, 0.335 mol) in methanol (1 L) was added ammonium formate (422.5 g, 6.7 mol), water (115 mL) and 65 g of palladium on activated carbon (10% on dry basis, ~50% wet with water; Degussa type E101NE/W) under a stream of $N_2$ while stirring via mechanical stirrer. After 24 and 48 hours, additional portions of ammonium formate (132 g, 2.1 mol) were added each time. Once reaction progression ceased, as monitored by anal. HPLC, Celite® (>500 g) was added and the resulting thick suspension was filtered and then the collected solid was rinsed with methanol (~500 mL). The filtrates were combined and concentrated under reduced pressure. The resulting cloudy, biphasic solution was then diluted with 1M phosphoric acid to a final volume of ~1.5 to 2.0 L at pH 2 and washed with dichloromethane (3×700 mL). The aqueous layer was basified to pH 12 using 40% aq. NaOH, and extracted with dichloromethane (3×700 mL). The combined organic layers were dried, filtered, and concentrated by rotary evaporation, then high-vacuum to provide the title intermediate (52 g), commonly N-Boc-endo-3-aminotropane, as a white to pale yellow solid. The isomer ratio of endo to exo amine of the product was >99:1 based on $^1$H-NMR analysis (>96% purity by analytical HPLC). $^1$H NMR (CDCl$_3$) δ (ppm) 4.2-4.0 (broad d, 2H, CHNBoc), 3.25 (t, 1H, CHNH$_2$), 2.1-2.05 (m, 4H), 1.9 (m, 2H), 1.4 s, 9H, (CH$_3$)$_3$OCON), 1.2-1.1 (broad, 2H). (m/z): [M+H]$^+$ calcd for C$_{12}$H$_{22}$N$_2$O$_2$ 227.18; found, 227.2. Analytical HPLC (isocratic method; 2:98 (A:B) to 90:10 (A:B) over 5 min): retention time=3.68 min.

EXAMPLE 1

Synthesis of 4-(tetrahydrofuran-2-carbonyl)piperazine-1-carboxylic acid 3-{(1S,3R,5R)-3-[(3-isopropyl-2-oxo-2,3-dihydrobenzoimidazole-1-carbonyl)amino]-8-aza-bicyclo[3.2.1]oct-8-yl}propyl ester

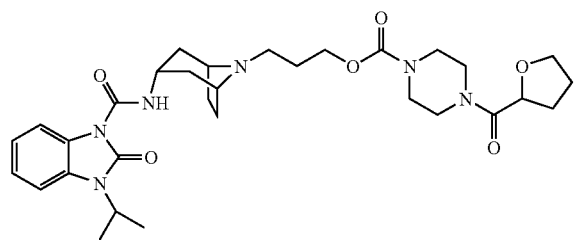

a. Preparation of (1S,3R,5R)-3-[(3-isopropyl-2-oxo-2,3-dihydrobenzoimidazole-1-carbonyl)amino]-8-azabicyclo[3.2.1]octane-8-carboxylic acid tert-butyl ester To a cold suspension of sodium hydride (9.25 g; 231.4 mmol; 60% dispersion in mineral oil) in dry THF (1000 L) in an ice bath was added the product of Preparation 1, 1-isopropyl-1,3-dihydro-2H-benzimidazol-2-one (27.2 g, 154.2 mmol), in THF (50 mL) under nitrogen atmosphere. The mixture was stirred at ~0-5° C. for 30 min, then 4-nitrophenyl chloroformate (34.2 g, 170 mmol) in THF (50 mL) was added. The mixture was stirred overnight while allowing the mixture to gradually warm to ambient temperature. To the activated ester formed was then added (1S,3R,5R)-3-amino-8-azabicyclo[3.2.1]octane-8-carboxylic acid tert-butyl ester (36.7 g, 162 mmol) in THF (50 mL). The mixture was stirred at ambient temperature for about 12 h, and at about 75° C. for about 3 h, at which time an LCMS of the reaction sample indicated completion of the coupling reaction. The mixture was concentrated in vacuo, dissolved in dichloromethane (1 L), and washed with first 1M H$_3$PO$_4$, and then saturated NaHCO$_3$ solution. After drying, the organic solution was evaporated to provide the title intermediate as a pale yellow residue that was used in the next step without further treatment.

b. Preparation of N-[(1S,3R,5R)-3-isopropyl-2-oxo-2,3-dihydrobenzoimidazole-1-carboxylic acid (8-azabicyclo[3.2.1]oct-3-yl)amide as a trifluoroacetate salt To a cold solution of (1S,3R,5R)-3-[(3-isopropyl-2-oxo-2,3-dihydrobenzoimidazole-1-carbonyl)amino]-8-azabicyclo[3.2.1]octane-8-carboxylic acid tert-butyl ester (the product of the previous step) in dichloromethane (200 mL) in an ice bath was added trifluoroacetic acid (200 mL). The mixture was stirred for about 30 min at ~5° C., and at room temperature for about 1 h. After evaporation of the mixture, ethyl ether (~500 mL) was added to the oily residue, causing solidification of the residue. The precipitate was collected, rinsed with copious amounts of ethyl ether, and dried in vacuo, to provide the title intermediate (47 g) as a TFA salt. The title intermediate is also commonly referred to as endo-N-(8-azabicyclo[3.2.1]oct-3-yl)-3-isopropyl-2-oxo-2,3-dihydrobenzimidazole-1-carboxamide.

c. Preparation of N-[(1S,3R,5R)-3-isopropyl-2-oxo-2,3-dihydrobenzoimidazole-11193-carboxylic acid (8-azabicyclo[3.2.1]oct-3-yl)amide (freebase)

To a suspension of the product of the previous step (15 g, 33.9 mmol) in dichloromethane (500 mL) was added water (500 mL). N,N-diisopropylethylamine (~20 mL) was added to the reaction mixture to bring the aqueous layer to a pH of 8-9. The layers were separated, retaining the organic layer. The aqueous layer was extracted a second time with dichloromethane (100 mL). The resulting extracts were combined, and then washed with brine. After drying over Na$_2$SO$_4$ and filtration, removal of the solvent yielded the title compound (9.7 g) as a freebase as a yellow powder. $^1$H NMR (DMSO-d$_6$): 1.48 (d, 6H), 1.40-2.00 (m, 8H), 3.53 (m, 2H), 4.07 (m, 1H), 4.69(septet, 1H), 7.21 (m, 2H), 7.45 (d, 1H), 8.08 (d, 1H), 9.31 (d, 1H). (m/z): [M+H]$^+$ calcd for C$_{18}$H$_{24}$N$_4$O$_2$ 329.20; found 329.2. Analytical HPLC: (2-50% MeCN/H$_2$O over 6 min) retention time=3.67 min.

d. Preparation of 3-chloropropyl-4-(tetrahydrofuran-2-ylcarbonyl)piperazine-1-carboxylate To a 0° C. solution of 1-(tetrahydrofuran-2-ylcarbonyl)piperazine (202 mg, 1.1 mmol) in dichloromethane (5 mL) was added 3-chloropropyl chloroformate (133 µL, 1.1 mmol) followed by N,N-diisopropylethylamine (192 µL, 1.1 mmol). The reaction was allowed to reach room temperature over 2 h, at which time the reaction was evaporated to yield the title compound as a wheat colored oil that was used without further purification.

e. Synthesis of 4-(tetrahydrofuran-2-carbonyl)piperazine-1-carboxylic acid 3-{(1S,3R,5R)-3-[(3-isopropyl-2-oxo-2,3-dihydrobenzoimidazole-1-carbonyl)amino]-8-aza-bicyclo[3.2.1]oct-8-yl}propyl ester 3-Chloropropyl-4-(tetrahydrofuran-2-ylcarbonyl)piperazine-1-carboxylate (335 mg, 1.1 mmol) was dissolved in dimethylformamide (5.0 mL) and added to the solid freebase product of step (c) (118 mg, 0.36 mmol) and NaI (164 mg, 0.72 mmol). N,N-diisopropylethylamine (64 µL, 0.36 mmol) was added and the mixture stirred at 90° C. overnight. Volatiles were removed and purification via prep HPLC (reverse phase) was accomplished on a gradient of 15-45% over 50 min; flow rate 20 mL/min to provide the title compound as a white solid as a TFA salt (45 mg). (m/z): [M+H]$^+$ calcd for $C_{31}H_{44}N_6O_6$ 597.33; found 597.1. Analytical HPLC: (5-65% MeCN/H$_2$O over 4 min) retention time=2.58.

EXAMPLE 2

Synthesis of 4-(2-hydroxyethyl)piperazine-1-carboxylic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester

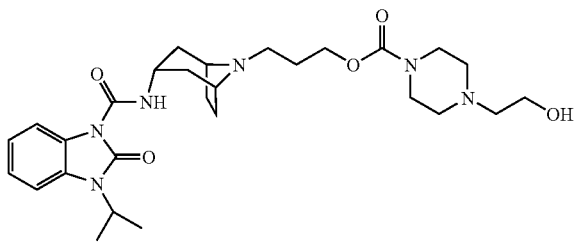

Using the processes described in Example 1, except in step (d) replacing 1-(tetrahydrofuran-2-ylcarbonyl)piperazine with 2-piperazin-1-ylethanol, the title compound (13.8 mg) was prepared as a TFA salt. (m/z): [M+H]$^+$ calcd for $C_{28}H_{42}N_6O_5$ 543.32; obsd. 543.5.

EXAMPLES 3-12

Using the processes described in Example 1, except in step (d) replacing 1-(tetrahydrofuran-2-ylcarbonyl)piperazine with the appropriate reagents, the following compounds of Examples 3-12 were prepared.

| Example | —NR$^3$R$^4$ | Formula | Calc. [M + H]$^+$ | Obs. [M + H]$^+$ |
|---|---|---|---|---|
| 3 | ![piperazine-acetyl] | $C_{28}H_{40}N_6O_5$ | 541.31 | 541.2 |
| 4 | ![piperidine-carbamate] | $C_{30}H_{44}N_6O_6$ | 585.33 | 585.2 |
| 5 | ![piperidine-carboxamide] | $C_{28}H_{40}N_6O_5$ | 541.31 | 541.2 |

-continued
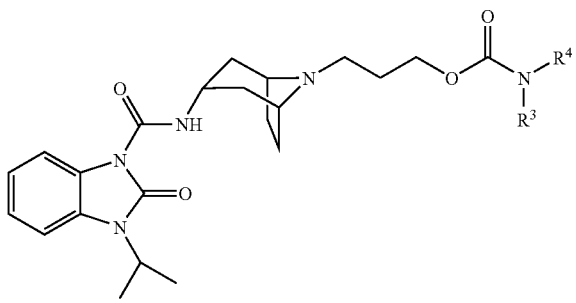
| Example | —NR³R⁴ | Formula | Calc. [M + H]⁺ | Obs. [M + H]⁺ |
|---|---|---|---|---|
| 6 | thiomorpholine dioxide | $C_{26}H_{37}N_5O_6S$ | 548.25 | 548.2 |
| 7 | N-methyl(tetrahydrothiophene dioxide)amine | $C_{27}H_{39}N_5O_6S$ | 562.26 | 562.2 |
| 8 | prolinamide | $C_{27}H_{38}N_6O_5$ | 527.29 | 527.2 |
| 9 | 4-acetyl-1,4-diazepane | $C_{29}H_{42}N_6O_5$ | 555.32 | 555.2 |
| 10 | N-methyl-N-(dimethylcarbamoylmethyl)amine | $C_{27}H_{40}N_6O_5$ | 529.31 | 529.2 |
| 11 | 4-(dimethylcarbamoyl)piperazine | $C_{29}H_{43}N_7O_5$ | 570.30 | 570.4 |
| 12 | 4-(dimethylsulfamoyl)piperazine | $C_{28}H_{43}N_7O_6S$ | 606.30 | 606.2 |

EXAMPLE 13

Alternative synthesis of 1,1-dioxo-1$\lambda^6$-thiomorpholine-4-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester

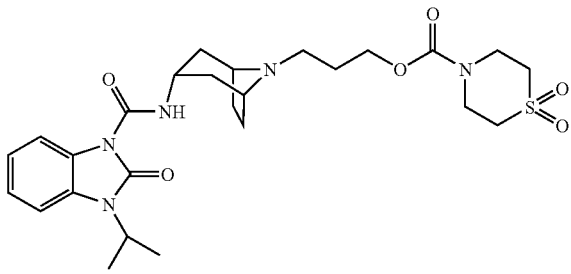

a. Preparation of (1S,3R,5R)-3-[(3-isopropyl-2-oxo-2,3-dihydrobenzoimidazole-1-carbonyl)amino]-8-azabicyclo[3.2.1]octane-8-carboxylic acid tert-butyl ester To a 500 mL reaction flask containing 1-isopropyl-1,3-dihydro-2H-benzimidazol-2-one (17.6 g, 100 mmol) and 4-nitrophenyl chloroformate (20.2 g, 100 mmol) under nitrogen atmosphere was added dichloromethane (350 mL) and then triethylamine (30.5 mL, 220 mmol) was added slowly. The solution was stirred for 15 min and then (1S,3R,5R)-3-amino-8-azabicyclo[3.2.1]octane-8-carboxylic acid tert-butyl ester (22.6 g, 100 mmol) was added. The reaction was allowed to stir overnight at room temperature. The reaction mixture was washed with aqueous saturated sodium bicarbonate (2×200 mL). Dichloromethane was removed by distillation and MTBE (350 mL) was added. The MTBE solution was washed with 1N phosphoric acid (2×200 mL), saturated sodium bicarbonate (200 mL), and water (200 mL). The organic layer was dried over anyhydrous sodium sulfate (40 g) and filtered, and then the solvent was removed by distillation to yield the title intermediate as a tan solid (35.7 g, 83% yield).

b. Preparation of N-[(1S,3R,5R)-3-isopropyl-2-oxo-2,3-dihydrobenzoimidazole-1-carboxylic acid (8-azabicyclo[3.2.1]oct-3-yl)amide trifluoroacetate salt In a 500 mL flask, (1S,3R,5R)-3-[(3-isopropyl-2-oxo-2,3-dihydrobenzoimidazole-1-carbonyl)amino]-8-azabicyclo[3.2.1]octane-8-carboxylic acid tert-butyl ester (21.4 g, 50 mmol) was dissolved in dichloromethane (200 mL). Trifluoroacetic acid (37 mL, 500 mmol) was added and the reaction mixture was allowed to stir at room temperature for 3 h. The reaction mixture was washed with water (2×100 mL). The solvent in the organic layer was removed by distillation and the crude product residue triturated by addition of MTBE (200 mL). After stirring for 1 h at room temperature, the solids were isolated by filtration, washed with MTBE (2×25 mL) and dried under vacuum to provide the title intermediate (21.0 g, 97% yield).

c. Preparation of 1,1-dioxo-1$\lambda^6$-thiomorpholine-4-carboxylic acid 3-chloropropyl ester In a 500 mL flask, thiomorpholine dioxide (13.5 g, 100 mmol) was dissolved in dichloromethane (150 mL) at room temperature and N,N-diisopropylethylamine (19.2 mL, 110 mmol) was added. After stirring at room temperature for 10 min, the reaction mixture was cooled in an ice bath to approximately 5° C. To the reaction mixture, was added 1-chloro-3-chloromethoxypropane (11.8 mL, 100 mmol) via addition funnel at a rate which maintained the reaction temperature below 10° C. When the addition was complete, the reaction mixture was allowed to warm to room temperature. The reaction mixture was washed with water (2×100 mL), and the organic phase dried over anhydrous sodium sulfate (25 g). After filtration, the solvent was removed by distillation to yield the title compound as an oily solid that solidified upon standing (24.0 g, 94% yield).

e. Synthesis of 1,1-dioxo-1$\lambda^6$-thiomorpholine-4-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester To a solution of N-[(1S,3R,5R)-3-isopropyl-2-oxo-2,3-dihydrobenzoimidazole-1-carboxylic acid (8-azabicyclo[3.2.1]oct-3-yl)amide trifluoroacetate salt (8.8 g, 20 mmol) in dichloromethane (100 mL) was added water (100 mL). The pH of the aqueous layer was adjusted to ~12 to provide the freebase of the salt. The organic layer was separated, dried over sodium sulfate and the solvent was removed by distillation. The freebase was dissolved in N-methyl-2-pyrrolidone (100 mL) and the solution transferred to a 250 mL flask containing 1,1-dioxo-1$\lambda^6$-thiomorpholine-4-carboxylic acid 3-chloropropyl ester (7.2 g, 28 mmol) and NaI (3.0 g, 20 mmol). N,N-diisopropylethylamine (4.2 mL, 24 mmol) was added and the reaction mixture was heated to 50° C. for 18 h. The solvent was removed by distillation. The crude product residue was dissolved in EtOAc (200 mL), washed with water (2×50 mL), and dried over sodium sulfate (10 g). The solvent was removed by distillation to afford crude product residue (~12 g).

The crude product residue was purified by preparative HPLC on a 2" column; packing: base-deactivated silica (BDS), flow rate: 200 mL/min; eluent A: 0.1% TFA in water; eluent B: 90% acetonitrile/10% 0.1% TFA in water; gradient (time, % B): (0, 5); (25, 30); (35, 80); (45, 80); (50,5); (60, 5). The product was isolated by lyophilization of the pure fractions to provide the title compound (3.4 g, 26% yield). $^1$H-NMR (DMSO-d$_6$) δ(ppm): 9.35 (d, 1H), 8.07 (d, 1H), 7.46 (d, 1H), 7.22 (t, 1H),7.16 (t, 1H), 4.69 (septet, 1H), 4.20-4.00 (m, 3H), 4.12 (t, 2H), 3.90-3.70 (m, 4H),370(t, 2H), 3.25-3.05 (m, 4H), 2.5-2.0 (m, 8H), 2.15 (dt, 2H), 1.49 (d, 6H). (m/z): [M+H]$^+$ calcd for C$_{26}$H$_{37}$N$_5$O$_6$S 548.2; found, 548.4

Assay 1: Radioligand Binding Assay on 5-HT$_{4(c)}$ Human Receptors a. Membrane Preparation 5-HT$_{4(c)}$ HEK-293 (human embryonic kidney) cells stably-transfected with human 5-HT$_{4(c)}$ receptor cDNA (Bmax=~6.0 pmol/mg protein, as determined using [$^3$H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS)

(GIBCO-Invitrogen Corp.: Cat #10437), 2 mM L-glutamine and (100 units) penicillin-(100 µg) streptomycin/ml (GIBCO-Invitrogen Corp.: Cat #15140) in a 5% $CO_2$, humidified incubator at 37° C. Cells were grown under continuous selection pressure by the addition of 800 µg/mL geneticin (GIBCO-Invitrogen Corp.: Cat #10131) to the medium.

Cells were grown to roughly 60-80% confluency (<35 subculture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −80° C.

b. Radioligand Binding Assays

Radioligand binding assays were performed in 1.1 mL 96-deep well polypropylene assay plates (Axygen) in a total assay volume of 400 µL containing 2 µg membrane protein in 50 mM HEPES pH 7.4, containing 0.025% bovine serum albumin (BSA). Saturation binding studies for determination of $K_d$ values of the radioligand were performed using [$^3$H]-GR113808 (Amersham Inc., Bucks, UK: Cat #TRK944; specific activity ~82 Ci/mmol) at 8-12 different concentrations ranging from 0.001 nM-5.0 nM. Displacement assays for determination of $pK_i$ values of compounds were performed with [$^3$H]-GR113808 at 0.15 nM and eleven different concentrations of compound ranging from 10 pM-100 µM.

Test compounds were received as 10 mM stock solutions in DMSO and diluted to 400 µM into 50 mM HEPES pH 7.4 at 25° C., containing 0.1% BSA, and serial dilutions (1:5) then made in the same buffer. Non-specific binding was determined in the presence of 1 µM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 µM GR113808. $K_i$ values for test compounds were calculated, in Prism, from the best-fit $IC_{50}$ values, and the $K_d$ value of the radioligand, using the Cheng-Prusoff equation (Cheng and Prusoff, *Biochemical Pharmacology*, 1973, 22, 3099-108): $K_i=IC_{50}/(1+[L]/K_d)$ where [L]=concentration [$^3$H]-GR113808. Results are expressed as the negative decadic logarithm of the $K_i$ values, $pK_i$.

Test compounds having a higher $pK_i$ value in this assay have a higher binding affinity for the 5-HT$_4$ receptor. The compounds of the invention which were tested in this assay had a $pK_i$ value ranging from about 7.0 to about 9.0, typically ranging from about 7.5 to about 8.5. For example, the compound of Example 1 exhibited a $pK_i$ value of 7.9 in this assay.

Assay 2: Radioligand Binding Assay on 5-HT$_{3A}$ Human Receptors: Determination of Receptor Subtype Selectivity a. Membrane Preparation 5-HT$_{3A}$ HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [$^3$H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #11965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 µg) streptomycin/ml (GIBCO-Invitrogen Corp.: Cat #15140) in a 5% $CO_2$, humidified incubator at 37° C.

Cells were grown to roughly 70-80% confluency (<35 subculture passages). All steps of the membrane preparation were performed on ice. To harvest the cells, the media was aspirated and cells were rinsed with $Ca^{2+}$, $Mg^{2+}$-free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 µL containing 1.5-2 µg membrane protein in 50 mM HEPES pH 7.4, containing 0.025% BSA assay buffer. Saturation binding studies for determination of $K_d$ values of the radioligand were performed using [$^3$H]-GR65630 (PerkinElmer Life Sciences Inc., Boston, Mass.: Cat #NET1011, specific activity ~85 Ci/mmol) at twelve different concentrations ranging from 0.005 nM to 20 nM. Displacement assays for determination of $pK_i$ values of compounds were performed with [$^3$H]-GR65630 at 0.50 nM and eleven different concentrations of compound ranging from 10 pM to 100 µM. Compounds were received as 10 mM stock solutions in DMSO (see section 3.1), diluted to 400 µM into 50 mM HEPES pH 7.4 at 25° C., containing 0.1% BSA, and serial (1:5) dilutions then made in the same buffer. Non-specific binding was determined in the presence of 10 µM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.)

was added to each well and plates were counted in a Packard Topcount liquid scintillation counter (Packard BioScience Co., Meriden, Conn.).

Binding data were analyzed using the non-linear regression procedure described above to determine $K_i$ values. The BOTTOM (curve minimum) was fixed to the value for nonspecific binding, as determined in the presence of 10 μM MDL72222. The quantity [L] in the Cheng-Prusoff equation was defined as the concentration [$^3$H]-GR65630.

Selectivity for the 5-HT$_4$ receptor subtype with respect to the 5-HT$_3$ receptor subtype was calculated as the ratio $K_i(5\text{-}HT_{3A})/K_i(5\text{-}HT_{4(c)})$. The compounds of the invention which were tested in this assay had a 5-HT$_4$/5-HT$_3$ receptor subtype selectivity ranging from about 10 to about 950, typically ranging from about 50 to about 500. For example, the compound of Example 1 exhibited a subtype selectivity of 160.

Assay 3: Whole-Cell cAMP Accumulation Flashplate Assay with HEK-293 Cells Expressing Human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture

HEK-293 (human embryonic kidney) cells stably-transfected with cloned human 5-HT$_{4(c)}$ receptor cDNA were prepared expressing the receptor at two different densities: (1) at a density of about 0.5-0.6 pmol/mg protein, as determined using a [$^3$H]-GR113808 membrane radioligand binding assay, and (2) at a density of about 6.0 pmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 μg) streptomycin/ml (GIBCO-Invitrogen Corp.: Cat #15140) in a 5% CO$_2$, humidified incubator at 37° C. Cells were grown under continuous selection pressure by the addition of geneticin (800 μg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 μm, flask yield was $1\text{-}2\times10^7$ cells/flask). Cells were resuspended at a concentration of $5\times10^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were $25\times10^3$ cells/well and the final assay volume was 100 μL. Test compounds were received as 10 mM stock solutions in DMSO, diluted to 400 μM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 pM to 100 μM (final assay concentrations). A 5-HT concentration-response curve (10 pM to 100 μM) was included on every plate. The cells were incubated, with shaking, at 37° C. for 15 min and the reaction terminated by addition of 100 μl of ice-cold detection buffer (as provided in the flashplate kit) to each well. The plates were sealed and incubated at 4° C. overnight. Bound radioactivity was quantified by scintillation proximity spectroscopy using the Topcount (Packard BioScience Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as pEC$_{50}$ values, the negative decadic logarithm of the EC$_{50}$ value, where EC$_{50}$ is the effective concentration for a 50% maximal response.

Test compounds exhibiting a higher pEC$_{50}$ value in this assay have a higher potency for agonizing the 5-HT$_4$ receptor. The compounds of the invention which were tested in this assay using cell line (1) having a density of about 0.5-0.6 pmol/mg protein, had a pEC$_{50}$ value in the range of about 7.5 to about 9.0, typically in the range of about 8.0 to about 9.0. For example, the compound of Example 1 had a pEC$_{50}$ value of 8.4.

Assay 4: In Vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F12 supplemented with 10% fetal bovine serum and 200 μg/mL geneticin. Cells were seeded onto poly-D-lysine (100 μg/mL) coated glass coverslips, in 35 mm$^2$ dishes (containing 2 mL medium) at a density that enabled isolated cells to be selected for whole cell voltage-clamp studies. The dishes were maintained in a humidified, 5% CO$_2$ environment at 37° C.

Extracellular solution was prepared at least every 7 days and stored at 4° C. when not in use. The extracellular solution contained (mM): NaCl (137), KCl (4), CaCl$_2$ (1.8), MgCl$_2$ (1), Glucose (10), 4-(2-hydroxyethyl)-1-piperazineethanesulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at −20° C. until the day of use. The intracellular solution contained (mM): KCl (130), MgCl$_2$ (1), ethylene glycol-bis(beta-aminoethyl ether) N,N,N',N'-tetra acetic acid salt (EGTA) (5), MgATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at −80 mV. After a stable whole-cell current was achieved, the cells were exposed to test compound. The standard voltage protocol was: step from the holding potential of −80 mV to +20 mV for 4.8 sec, repolarize to −50 mV for 5 sec and then return to the original holding potential (−80 mV). This voltage protocol was run once every 15 sec (0.067 Hz). Peak current amplitudes during the repolarization phase were determined using pClamp software. Test compounds at a concentration of 3 µM were perfused over the cells for 5 minutes, followed by a 5-minute washout period in the absence of compound. Finally a positive control (cisapride, 20 nM) was added to the perfusate to test the function of the cell. The step from −80 mV to +20 mV activates the hERG channel, resulting in an outward current. The step back to −50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed $K^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at $p<0.05$.

The smaller the percentage inhibition of the potassium ion current in this assay, the smaller the potential for test compounds to change the pattern of cardiac repolarization when used as therapeutic agents. The compounds of the invention which were tested in this assay at a concentration of 3 µM typically exhibited an inhibition of the potassium ion current of less than about 40%, more typically, less than about 25%. For example, the compound of Example 1 exhibited an inhibition of about 9% in this assay.

Assay 5: In Vitro Model of Oral Bioavailability: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

Caco-2 (colon, adenocarcinoma; human) cells were obtained from ATCC (American Type Culture Collection; Rockville, Md.). For the permeation study, cells were seeded at a density of 63,000 cells/cm² on pre-wetted transwells polycarbonate filters (Costar; Cambridge, Mass.). A cell monolayer was formed after 21 days in culture. Following cell culture in the transwell plate, the membrane containing the cell monolayer was detached from the transwell plate and inserted into the diffusion chamber (Costar; Cambridge, Mass.). The diffusion chamber was inserted into the heating block which was equipped with circulating external, thermostatically regulated 37° C. water for temperature control. The air manifold delivered 95% $O_2$/5% $CO_2$ to each half of a diffusion chamber and created a laminar flow pattern across the cell monolayer, which was effective in reducing the unstirred boundary layer.

The permeation study was performed with test compound concentrations at 100 µM and with $^{14}C$-mannitol to monitor the integrity of the monolayer. All experiments were conducted at 37° C. for 60 min. Samples were taken at 0, 30 and 60 min from both the donor and receiver sides of the chamber. Samples were analyzed by HPLC or liquid scintillation counting for test compound and mannitol concentrations. The permeation coefficient ($K_p$) in cm/sec was calculated.

In this assay, a $K_p$ value greater than about $10 \times 10^{-6}$ cm/sec is considered indicative of favorable bioavailability. The compounds of the invention that were tested in this assay typically exhibited $K_p$ values of between about $20 \times 10^{-6}$ cm/sec and about $60 \times 10^{-6}$ cm/sec, more typically between about $30 \times 10^{-6}$ cm/sec and about $60 \times 10^{-6}$ cm/sec. For example, the compound of Example 1 exhibited a $K_p$ value of $60 \times 10^{-6}$ cm/sec.

Assay 6: Pharmacokinetic Study in the Rat

Aqueous solution formulations of test compounds were prepared in 0.1% lactic acid at a pH of between about 5 and about 6. Male Sprague-Dawley rats (CD strain, Charles River Laboratories, Wilmington, Mass.) were dosed with test compounds via intravenous administration (IV) at a dose of 2.5 mg/kg or by oral gavage (PO) at a dose of 5 mg/kg. The dosing volume was 1 mL/kg for IV and 2 mL/kg for PO administration. Serial blood samples were collected from animals pre-dose, and at 2 (IV only), 5, 15, and 30 min, and at 1, 2, 4, 8, and 24 hours post-dose. Concentrations of test compounds in blood plasma were determined by liquid chromatography-mass spectrometry analysis (LC-MS/MS) (MDS SCIEX, API 4000, Applied Biosystems, Foster City, Calif.) with a lower limit of quantitation of 1 ng/mL.

Standard pharmacokinetic parameters were assessed by non-compartmental analysis (Model 201 for IV and Model 200 for PO) using WinNonlin (Version 4.0.1, Pharsight, Mountain View, Calif.). The maximum in the curve of test compound concentration in blood plasma vs. time is denoted $C_{max}$. The area under the concentration vs. time curve from the time of dosing to the last measurable concentration (AUC(0-t)) was calculated by the linear trapezoidal rule. Oral bioavailability (F(%)), i.e. the dose-normalized ratio of AUC(0-t) for PO administration to AUC(0-t) for IV administration, can be calculated as:

$$F(\%) = AUC_{PO}/AUC_{IV} \times Dose_{IV}/Dose_{PO} \times 100\%$$

Test compounds which exhibit larger values of the parameters $C_{max}$, AUC(0-t), and F(%) in this assay are expected to have greater bioavailability when administered orally. The compounds of the invention that were tested in this assay had $C_{max}$ values between about 0.15 to about 0.35 µg/mL and AUC(0-t) values between about 0.5 to about 1.1 µg·hr/mL. In particular, the compound of Example 1 had the following values: $C_{max}$ of 0.32 µg/mL; AUC(0-t) of 0.97 µg·hr/mL; and oral bioavailability F(%) of 55%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Additionally, all publications, patents, and patent documents cited hereinabove are incorporated by reference herein in full, as though individually incorporated by reference.

What is claimed is:

1. A compound of formula (I):

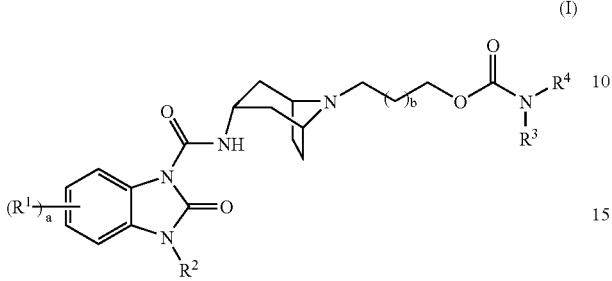

wherein:
R$^1$ is halo or C$_{1-3}$alkyl, wherein C$_{1-3}$alkyl is optionally substituted with hydroxy or halo;
R$^2$ is hydrogen or C$_{1-3}$alkyl, wherein C$_{1-3}$alkyl is optionally substituted with hydroxy;
R$^3$ is C$_{1-3}$alkyl or hydrogen;
R$^4$ is —(CH$_2$)$_{1-3}$C(O)NR$^a$R$^b$,

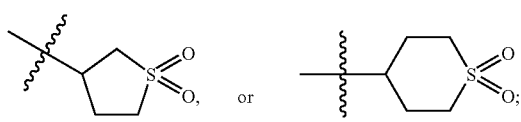

or R$^3$ and R$^4$ together with the nitrogen atom to which they are attached form a moiety selected from:
(i) a moiety of formula (a):

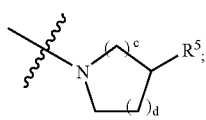

(ii) a moiety of formula (b):

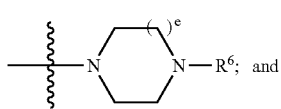

(iii) a moiety of formula (c):

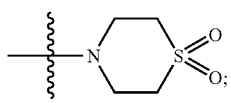

wherein:
R$^5$ is —OC(O)NR$^a$R$^b$, —C(O)NR$^a$R$^b$, —NR$^d$S(O)$_2$C$_{1-3}$alkyl, —NR$^d$C(O)R$^c$, —NR$^d$S(O)$_2$NR$^a$R$^b$, or —NR$^d$C(O)OR$^e$;
R$^6$ is —C(O)R$^f$, —(CH$_2$)$_2$OR$^g$, —S(O)$_2$NR$^a$R$^b$, —S(O)$_2$C$_{1-3}$alkyl, or —S(O)$_2$(CH$_2$)$_{1-3}$S(O)$_2$C$_{1-3}$alkyl;
R$^a$, R$^b$, and R$^c$ are independently hydrogen or C$_{1-3}$alkyl;
R$^d$ is hydrogen or C$_{1-3}$alkyl, wherein C$_{1-3}$alkyl is optionally substituted with hydroxy;

R$^e$ is C$_{1-3}$alkyl;
R$^f$ is hydrogen, C$_{1-3}$alkyl, tetrahydrofuranyl, or —NR$^a$R$^b$;
R$^g$ is hydrogen or C$_{1-3}$alkyl;
a is 0, 1 or 2;
b is 0, 1, 2 or 3;
c is 0, 1, or 2;
d is 1 or 2; and
e is 1 or 2;
provided that when c is 0, then d is 2, and R$^5$ is —C(O)NR$^a$R$^b$; and when c is 2, then d is 1;
or a pharmaceutically-acceptable salt or solvate or stereoisomer thereof.

2. The compound of claim 1, wherein a is 0.

3. The compound of claim 1, wherein R$^2$ is ethyl or isopropyl.

4. The compound of claim 1, wherein b is 1.

5. The compound of claim 1, wherein R$^3$ and R$^4$ together with the nitrogen atom to which they are attached form a moiety of formula (b).

6. The compound of claim 1, wherein R$^3$ and R$^4$ together with the nitrogen atom to which they are attached form a moiety of formula (c).

7. The compound of claim 1, wherein:
R$^2$ is ethyl or isopropyl;
R$^3$ is C$_{1-3}$alkyl; and
R$^4$ is —(CH$_2$)$_{1-3}$C(O)NR$^a$R$^b$ or

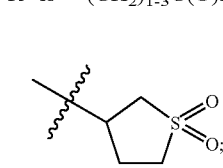

or R$^3$ and R$^4$ together with the nitrogen atom to which they are attached form a moiety selected from a moiety of formula (a), a moiety of formula (b), and a moiety of formula (c);
wherein R$^5$ is —OC(O)NR$^a$R$^b$ or —C(O)NR$^a$R$^b$;
R$^6$ is —C(O)R$^f$, —(CH$_2$)$_2$OR$^g$, or —S(O)$_2$NR$^a$R$^b$;
R$^a$, R$^b$, and R$^g$ are independently hydrogen or methyl;
R$^f$ is methyl, tetrahydrofuranyl, or —NR$^a$R$^b$;
a is 0;
b is 1;
c is 1 or 2;
d is 1; and
e is 1.

8. The compound of claim 7, wherein R$^3$ and R$^4$ together with the nitrogen atom to which they are attached form a moiety of formula (b), wherein R$^6$ is —C(O)R$^f$.

9. The compound of claim 1, wherein the compound is selected from:
4-(tetrahydrofuran-2-carbonyl)piperazine-1-carboxylic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester;
4-(2-hydroxyethyl)piperazine-1-carboxylic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester;
4-acetyl-piperazine-1-carboxylic acid 3-{(1S,3R,5R)-3-[(3-isopropyl-2-oxo-2,3-dihydro-benzoimidazole-1-carbonyl)amino]-8-azabicyclo[3.2.1]oct-8-yl}propyl ester;

4-dimethylcarbamoyloxypiperidine-1-carboxylic acid 3-{(1S,3R,5R)-3-[(3-isopropyl-2-oxo-2,3-dihydrobenzoimidazole-1-carbonyl)amino]-8-aza-bicyclo[3.2.1]oct-8-yl}propyl ester;

3-carbamoylpiperidine-1-carboxylic acid 3-{(1S,3R,5R)-3-[(3-isopropyl-2-oxo-2,3-dihydro-benzoimidazole-1-carbonyl)amino]-8-azabicyclo[3.2.1]oct-8-yl}propyl ester;

1,1-dioxo-1λ$^6$-thiomorpholine-4-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester;

(1,1-dioxotetrahydro-1λ$^6$-thiophen-3-yl)methylcarbamic acid 3-{(1S,3R,5R)-3-[(3-isopropyl-2-oxo-2,3-dihydrobenzoimidazole-1-carbonyl)amino]-8-azabicyclo-[3.2.1]oct-8-yl}propyl ester;

(R)-2-carbamoylpyrrolidine-1-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester;

4-acetyl-[1,4]diazepane-1-carboxylic acid 3-{(1S,3R,5R)-3-[(3-isopropyl-2-oxo-2,3-dihydro-benzoimidazole-1-carbonyl)amino]-8-azabicyclo[3.2.1]oct-8-yl}propyl ester;

dimethylcarbamoylmethyl-methylcarbamic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester;

4-dimethylcarbamoylpiperazine-1-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester; and 4-dimethylsulfamoylpiperazine-1-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester; and pharmaceutically-acceptable salts or solvates or stereoisomers thereof.

10. The compound of claim 1 where in the compound is 1,1-dioxo-1λ$^6$-thiomorpholine-4-carboxylic acid 3-{(1S,3R,5R)-3-[(3-isopropyl-2-oxo-2,3-dihydrobenzoimidazole-1-carbonyl)amino]-8-azabicyclo[3.2.1]oct-8-yl}propyl ester or a pharmaceutically-acceptable salt or solvate or stereoisomer thereof.

11. A pharmaceutical composition comprising a therapeutically effective amount of the compound of claim 1 and a pharmaceutically acceptable carrier.

12. A pharmaceutical composition comprising a therapeutically effective amount of the compound of claim 10 and a pharmaceutically acceptable carrier.

13. A process for preparing a compound of formula (I):

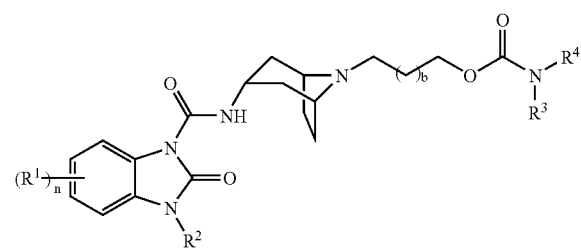

wherein:

$R^1$ is halo or $C_{1-3}$alkyl, wherein $C_{1-3}$alkyl is optionally substituted with hydroxy or halo;

$R^2$ is hydrogen or $C_{1-3}$alkyl, wherein $C_{1-3}$alkyl is optionally substituted with hydroxy;

$R^3$ is $C_{1-3}$alkyl or hydrogen;

$R^4$ is —$(CH_2)_{1-3}C(O)NR^aR^b$,

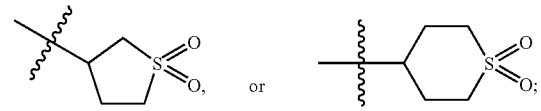

or $R^3$ and $R^4$ together with the nitrogen atom to which they are attached form a moiety selected from:

(i) a moiety of formula (a):

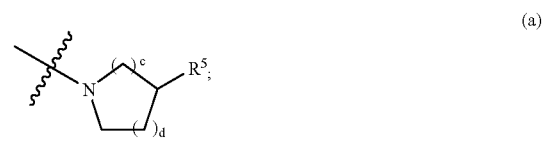

(ii) a moiety of formula (b):

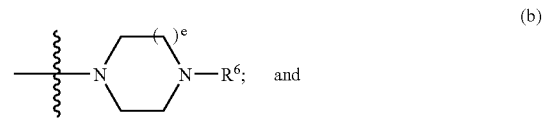

(iii) a moiety of formula (c):

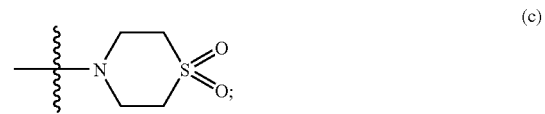

wherein:

$R^5$ is —$C(O)NR^aR^b$, —$C(O)NR^aR^b$, —$NR^dS(O)_2C_{1-3}$alkyl, —$NR^dC(O)R^c$, —$NR^dS(O)_2NR^aR^b$, or —$NR^dC(O)OR^e$;

$R^6$ is —$C(O)R^f$, —$(CH_2)_2OR^g$, —$S(O)_2NR^aR^b$, —$S(O)_2C_{1-3}$alkyl, or —$S(O)_2(CH_2)_{1-3}S(O)_2C_{1-3}$alkyl;

$R^a$, $R^b$, and $R^c$ are independently hydrogen or $C_{1-3}$alkyl;

$R^d$ is hydrogen or $C_{1-3}$alkyl, wherein $C_{1-3}$alkyl is optionally substituted with hydroxy;

$R^e$ is $C_{1-3}$alkyl;

$R^f$ is hydrogen, $C_{1-3}$alkyl, tetrahydrofuranyl, or —$NR^aR^b$;

$R^g$ is hydrogen or $C_{1-3}$alkyl;

a is 0, 1 or 2;

b is 0, 1, 2 or 3;

c is 0, 1, or 2;

d is 1 or 2; and e is 1 or 2;

provided that when c is 0, then d is 2, and $R^5$ is —$C(O)NR^aR^b$; and when c is 2, then d is 1;

or a pharmaceutically-acceptable salt or solvate or stereoisomer thereof, the process comprising:

(a) reacting a compound of formula (III):

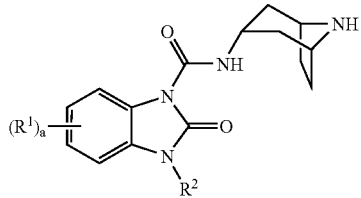

(III)

with a compound of formula (IV):

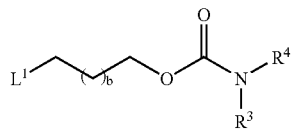

(IV)

wherein $L^1$ is a leaving group; or (b) reacting a compound of formula (V):

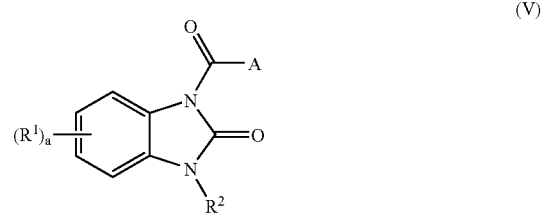

(V)

wherein A is a leaving group;
with a compound of formula (VI):

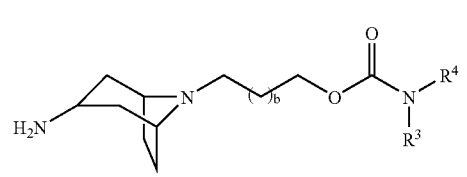

(VI)

to provide a compound of formula (I), or a pharmaceutically-acceptable salt or solvate or stereoisomer thereof.

* * * * *

UNITED STATES PATENT AND TRADEMARK OFFICE
CERTIFICATE OF CORRECTION

PATENT NO. : 7,329,752 B2
APPLICATION NO. : 11/602888
DATED : February 12, 2008
INVENTOR(S) : Long et al.

It is certified that error appears in the above-identified patent and that said Letters Patent is hereby corrected as shown below:

Column 45,
Lines 56-65, Claim 13, the formula structure should be

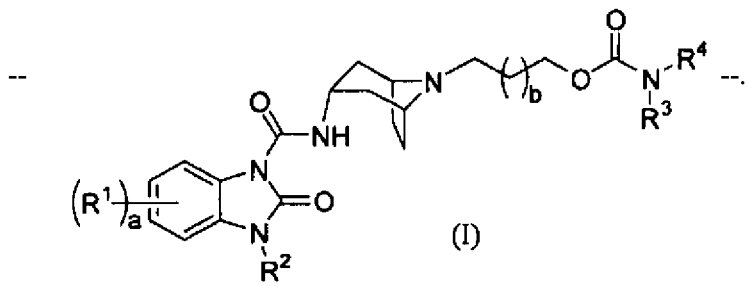

Column 46,
Line 47, "-C(O)NR$^a$R$^{b}$" should be -- -OC(O)NR$^a$R$^b$ --.

Signed and Sealed this

Thirtieth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,329,752 B2  Page 1 of 1
APPLICATION NO. : 11/602888
DATED : February 12, 2008
INVENTOR(S) : Daniel D. Long et al.

It is certified that error appears in the above-identified patent and that said Letters Patent is hereby corrected as shown below:

Column 5,
line 50, the structure:

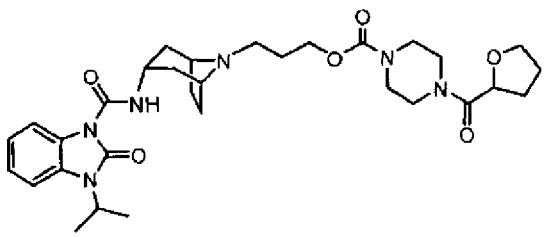

should appear as:

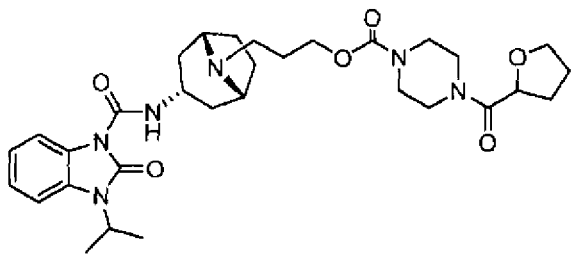

Signed and Sealed this

First Day of September, 2009

David J. Kappos
*Director of the United States Patent and Trademark Office*